US008176768B2

(12) United States Patent
Kondo et al.

(10) Patent No.: US 8,176,768 B2
(45) Date of Patent: May 15, 2012

(54) PARTICULATE MATTER DETECTION DEVICE

(75) Inventors: Atsuo Kondo, Nagoya (JP); Takeshi Sakuma, Nagoya (JP); Takashi Egami, Nagoya (JP); Tatsuya Okayama, Wako (JP); Masanobu Miki, Wako (JP); Keizo Iwama, Wako (JP)

(73) Assignees: NGK Insulators, Ltd., Nagoya (JP); Honda Motor Co., Ltd., Minato-Ku (JP)

( * ) Notice: Subject to any disclaimer, the term of this patent is extended or adjusted under 35 U.S.C. 154(b) by 446 days.

(21) Appl. No.: 12/493,280

(22) Filed: Jun. 29, 2009

(65) Prior Publication Data

US 2010/0000863 A1    Jan. 7, 2010

(30) Foreign Application Priority Data

Jul. 4, 2008    (JP) ................. 2008-176075
Jul. 4, 2008    (JP) ................. 2008-176080
Jul. 4, 2008    (JP) ................. 2008-176082
Jan. 28, 2009   (JP) ................. 2009-016412

(51) Int. Cl.
*G01N 15/06* (2006.01)

(52) U.S. Cl. ............. 73/23.33; 73/31.02; 73/31.03; 73/31.05; 73/31.06

(58) Field of Classification Search ........... 73/23.2, 73/23.3, 23.31–23.34, 28.01, 28.02, 31.01–31.03, 73/31.05, 31.06
See application file for complete search history.

(56) References Cited

U.S. PATENT DOCUMENTS

| 4,413,502 | A  | * | 11/1983 | Ohta et al. ............... 73/23.31 |
| 5,008,628 | A  | * | 4/1991  | Krigmont et al. ......... 324/693 |
| 5,018,380 | A  | * | 5/1991  | Zupancic et al. .......... 73/23.2 |
| 5,922,946 | A  | * | 7/1999  | Hirota et al. ............. 73/61.75 |
| 6,634,210 | B1 | * | 10/2003 | Bosch et al. ............. 73/23.33 |
| 6,904,787 | B2 |   | 6/2005  | Totoki |
| 7,541,004 | B2 | * | 6/2009  | Niksa et al. ............. 422/82.02 |
| 7,543,477 | B2 | * | 6/2009  | Berger et al. ............ 73/23.33 |
| 7,886,578 | B2 |   | 2/2011  | Schmidt et al. |
| 7,891,232 | B2 | * | 2/2011  | Hall ....................... 73/28.01 |
| 8,015,862 | B2 | * | 9/2011  | Bollinger et al. ......... 73/114.69 |

(Continued)

FOREIGN PATENT DOCUMENTS

DE    10 2006 047 927 A1    4/2008

(Continued)

OTHER PUBLICATIONS

Japanese Office Action dated Feb. 7, 2012 (English translation only).

*Primary Examiner* — David Rogers
(74) *Attorney, Agent, or Firm* — Burr & Brown

(57) ABSTRACT

A particulate matter detection device 100 includes a first electrode 1 whose one surface is covered with an inter-electrode dielectric material 4; a second electrode 2 disposed on the side of the one surface of the first electrode 1, to perform the discharge of electricity by a voltage applied between the first electrode 1 and the second electrode; and a pair of measurement electrodes 5, 15 disposed on the surface of the inter-electrode dielectric material 4 so as to face each other; characteristic measurement means 3 for measuring electric characteristics between the pair of measurement electrodes 5 and 15; and particulate matter amount calculation means 13 for obtaining the amount of the particulate matter 11 collected by the surface of the inter-electrode dielectric material 4, based on the change amount of the electric characteristics.

20 Claims, 23 Drawing Sheets

U.S. PATENT DOCUMENTS

| | | | |
|---|---|---|---|
| 8,033,159 B2 * | 10/2011 | Fleischer et al. | 73/28.01 |
| 2001/0051108 A1 * | 12/2001 | Schonauer | 422/68.1 |
| 2004/0035758 A1 * | 2/2004 | Yoshiyama et al. | 209/129 |
| 2005/0126260 A1 * | 6/2005 | Totoki | 73/31.02 |
| 2005/0279084 A1 | 12/2005 | Schmidt et al. | |
| 2007/0119233 A1 * | 5/2007 | Schnell et al. | 73/28.01 |
| 2007/0264158 A1 | 11/2007 | Schmidt et al. | |
| 2008/0105567 A1 | 5/2008 | Okayama et al. | |
| 2008/0265870 A1 * | 10/2008 | Nair et al. | 324/105 |
| 2009/0056416 A1 * | 3/2009 | Nair et al. | 73/28.01 |
| 2009/0090622 A1 * | 4/2009 | Ripley | 204/401 |
| 2009/0309571 A1 * | 12/2009 | Katsuyama et al. | 324/71.1 |
| 2010/0147052 A1 * | 6/2010 | Nelson et al. | 73/28.01 |
| 2010/0192670 A1 * | 8/2010 | Schaenzlin et al. | 73/23.31 |

FOREIGN PATENT DOCUMENTS

| | | | |
|---|---|---|---|
| EP | 2120044 A1 * | 11/2009 | |
| JP | 60-123761 A1 | 7/1985 | |
| JP | 63-286753 | 11/1988 | |
| JP | 63-286753 A1 | 11/1998 | |
| JP | 2003-315244 A1 | 11/2003 | |
| JP | 2008-051715 A1 | 3/2008 | |
| JP | 2008-512661 A1 | 4/2008 | |
| JP | 2008-139294 A1 | 6/2008 | |
| JP | 2009-186278 | 8/2009 | |
| WO | 2007/000368 | 1/2007 | |
| WO | 2008/111677 | 9/2008 | |

\* cited by examiner

AMOUNT OF DEPOSITED PM

PM CONCENTRATION

PARTICULATE MATTER DETECTION DEVICE

BACKGROUND OF THE INVENTION

1. Field of the Invention

The present invention relates to a device which detects a particulate matter included in an exhaust gas from a diesel engine or the like.

2. Description of the Related Art

An exhaust gas from a diesel engine or the like includes a particulate matter (PM) detected as three components, that is, an organic solvent soluble component, soot and sulfate, which causes air pollution. In particular, when a defect occurs in a particulate matter generation source such as the diesel engine, the particulate matter in the exhaust gas discharged to the atmosphere increases, and noticeably adversely affects the environment. For the prevention of this problem, it is essential to detect the particulate matter in the exhaust gas and recognize the defect of the diesel engine or the like.

Moreover, in recent years, to prevent environmental pollution and improve the environment, a diesel particulate filter (DPF) for the treatment of the exhaust gas is incorporated and used in an exhaust system or the like. This DPF is generally made of a ceramic material, and can be used with high reliability for a long time. However, it cannot be considered that there is not any possibility that a defect such as a crack is generated owing to thermal deterioration or the like. If the defect is generated, a small amount of particulate matter might leak. For the prevention of this problem, it is important to detect the particulate matter in the exhaust gas treated with the DPF and immediately detect the generation of the defect.

It is to be noted that examples of prior documents include Patent Document 1 (JP-A-60-123761). In Patent Document 1, a particulate matter detection device is disclosed which electrically charges the particulate matter by corona discharge and which measures the ion current of the particulate matter to measure the amount of the particulate matter.

SUMMARY OF THE INVENTION

However, in a method described in Patent Document 1, a particulate matter is electrically charged with a weak ion current, and a large-scaled detection circuit for detecting such a weak ion current is required, whereby a device becomes expensive. In addition, when the flow rate of an exhaust gas is large, the particulate matter cannot effectively electrically be charged, and a measured value becomes smaller than the amount of the particulate matter actually included in the exhaust gas. Therefore, there is a room for the improvement of accuracy.

The present invention has been developed in view of such a situation, and an object thereof is to provide a particulate matter detection device which can easily detect the particulate matter and which is inexpensive and which has a high measurement accuracy. As a result of repeated investigations, it has been found that the following means can solve this problem.

That is, according to the present invention, there is provided a particulate matter detection device (hereinafter referred to as the first particulate matter detection device) comprising: a first electrode which has a plate-like shape and whose one surface is covered with a dielectric material (referred to as the inter-electrode dielectric material); a second electrode (forming a pair with the first electrode and) disposed on the side of the one surface of the first electrode (covered with the inter-electrode dielectric material) via a space through which a gas including a particulate matter flows, to perform the formation of an electric field and/or the discharge of electricity by a voltage applied between the first electrode and the second electrode; and a power source for dust collection which applies the voltage; and a pair of measurement electrodes disposed on the surface of the dielectric material (the inter-electrode dielectric material) so as to face each other; characteristic measurement means for measuring electric characteristics between the pair of measurement electrodes; and particulate matter amount calculation means for obtaining the amount of the particulate matter collected by the surface of the dielectric material (the inter-electrode dielectric material) based on the change amount of the electric characteristics measured by the characteristic measurement means.

The first particulate matter detection device according to the present invention preferably further comprises a flow rate meter which measures or estimates the flow rate of the gas flowing through the space; and particulate matter concentration calculation means for calculating the concentration of the particulate matter in the gas flowing through the space based on the flow rate of the gas measured or estimated by the flow rate meter and the amount of the particulate matter.

In the first particulate matter detection device according to the present invention, the electric characteristics are preferably one or more electric characteristics selected from the electric characteristic group consisting of a resistance, an inductance, a capacitance and an impedance.

In the first particulate matter detection device according to the present invention, the pair of measurement electrodes preferably have a linear shape and are disposed on the surface of the dielectric material (the inter-electrode dielectric material) so as to be long in a direction vertical to a direction in which the gas including the particulate matter flows and so as to face each other. In this case, each of the pair of measurement electrodes having the linear shape is preferably branched into a plurality of electrodes, respectively, and has a plurality of facing portions. Further in this case, the pair of measurement electrodes having the plurality of facing portions are preferably disposed over the whole surface of the dielectric material (the inter-electrode dielectric material).

In the first particulate matter detection device according to the present invention, the second electrode preferably has a plate-like shape. In this case, the second electrode is preferably constituted of a tubular wall surface.

In the first particulate matter detection device according to the present invention, the second electrode preferably has a needle-like or rod-like shape.

The first particulate matter detection device according to the present invention preferably further comprises a dielectric material (hereinafter referred to as the off-electrode dielectric material) which covers the other surface of the first electrode having the plate-like shape; and a heater disposed on the surface of the dielectric material (the off-electrode dielectric material).

The first particulate matter detection device according to the present invention preferably further comprises a power source for removal which applies a voltage between the first electrode and the pair of measurement electrodes, wherein the voltage is applied to perform the discharge of the electricity along the surface of the dielectric material (the inter-electrode dielectric material) which covers the one surface of the first electrode.

In the first particulate matter detection device according to the present invention, the measurement electrodes are preferably covered with a film-like dielectric material.

The first particulate matter detection device according to the present invention preferably further comprises a detection device main body constituted of a dielectric material provided with, in one end thereof, a through hole as the space through which the gas including the particulate matter flows, the dielectric material being long in one direction, wherein the first electrode and the second electrode are embedded in the detection device main body so as to sandwich the through hole therebetween while the one surface of the first electrode faces the side of the through hole, and the pair of measurement electrodes are disposed on the inner wall surface of the through hole in which the first electrode is embedded.

In the first particulate matter detection device according to the present invention, the other end of the detection device main body is preferably provided with a takeoff terminal of at least one of the first electrode and the second electrode.

In the first particulate matter detection device according to the present invention, at least one heater is preferably embedded in a position of at least one of the first electrode and the second electrode on a side opposite to the side on which the through hole is formed.

Next, according to the present invention, there is provided a particulate matter detection device (hereinafter referred to as the second particulate matter detection device) comprising: a first electrode which has a plate-like shape and whose one surface is covered with a dielectric material (an inter-electrode dielectric material); a second electrode disposed on the side of the one surface of the first electrode via a space through which a gas including a particulate matter flows, to perform the formation of an electric field and/or the discharge of electricity by a voltage applied between the first electrode and the second electrode; and a power source which applies the voltage; and a measurement counter electrode disposed on the surface of the dielectric material (the inter-electrode dielectric material); characteristic measurement means for measuring electric characteristics between the measurement counter electrode and the first electrode; and particulate matter amount calculation means for obtaining the amount of the particulate matter collected by the surface of the dielectric material (the inter-electrode dielectric material) based on the change amount of the electric characteristics measured by the characteristic measurement means.

The second particulate matter detection device according to the present invention preferably further comprises a flow rate meter which measures or estimates the flow rate of the gas flowing through the space; and particulate matter concentration calculation means for calculating the concentration of the particulate matter in the gas flowing through the space based on the flow rate of the gas measured or estimated by the flow rate meter and the amount of the particulate matter.

In the second particulate matter detection device according to the present invention, the electric characteristics are preferably one or more electric characteristics selected from the electric characteristic group consisting of a resistance, an inductance, a capacitance and an impedance.

In the second particulate matter detection device according to the present invention, the measurement counter electrode preferably has a plurality of linear portions, and the plurality of linear portions are disposed on the surface of the dielectric material (the inter-electrode dielectric material) so as to be long in parallel with a direction vertical to a direction in which the gas including the particulate matter flows. In this case, the measurement counter electrode having the plurality of linear portions preferably has a lattice-like shape. That is, the plurality of linear portions include portions disposed so as to be long in parallel with the direction vertical to the direction in which the gas including the particulate matter flows and portions disposed so as to be long in parallel with the same direction as the direction in which the gas including the particulate matter flows, to form the lattice-like shape. Further in this case, the measurement counter electrode having the plurality of linear portions is preferably disposed over the whole surface of the dielectric material (the inter-electrode dielectric material).

In the second particulate matter detection device according to the present invention, the second electrode preferably has a plate-like shape. In this case, the second electrode is preferably constituted of a tubular wall surface. That is, the second electrode is formed into a tubular shape constituted of a curved surface by rounding a plate-like material, and specifically corresponds to the whole surface or one surface of an exhaust tube.

In the second particulate matter detection device according to the present invention, the second electrode preferably has a needle-like or rod-like shape.

The second particulate matter detection device according to the present invention preferably further comprises a dielectric material (an off-electrode dielectric material) which covers the other surface of the first electrode having the plate-like shape; and a heater disposed on the surface of the dielectric material (the off-electrode dielectric material).

The second particulate matter detection device according to the present invention preferably further comprises a power source for removal which applies a voltage between the first electrode and the measurement counter electrode to oxidize and remove the particulate matter by the discharge of electricity along the surface, wherein the voltage is applied to perform the discharge of the electricity along the surface of the dielectric material (the inter-electrode dielectric material) which covers the one surface of the first electrode.

In the second particulate matter detection device according to the present invention, the measurement counter electrode is preferably covered with a film-like dielectric material.

Next, according to the present invention, there is provided a particulate matter detection device (hereinafter referred to as the third particulate matter detection device) comprising: a first electrode which has a plate-like shape and whose one surface is covered with a planar dielectric material (an inter-electrode dielectric material); a second electrode disposed on the side of the one surface of the first electrode via a space through which a gas including a particulate matter flows, to perform the formation of an electric field and/or the discharge of electricity by a voltage applied between the first electrode and the second electrode; and a power source which applies the voltage; and a measurement counter electrode disposed on the surface of a protruding dielectric material (a stepped base dielectric material) provided on the surface of the planar dielectric material (the inter-electrode dielectric material) and having a stepped portion with respect to the planar dielectric material (the inter-electrode dielectric material); characteristic measurement means for measuring electric characteristics between the measurement counter electrode and the first electrode; and particulate matter amount calculation means for obtaining the amount of the particulate matter collected by the formation of the electric field and/or the discharge of the electricity, based on the change amount of the electric characteristics measured by the characteristic measurement means.

The particulate matter detection device according to the present invention simply mentioned in the present description include all of the first particulate matter detection device, the second particulate matter detection device and the third particulate matter detection device.

In the third particulate matter detection device according to the present invention, as described above, the protruding dielectric material for disposing the measurement counter electrode thereon will also be referred to as the stepped base dielectric material. This protruding dielectric material is apparently similar to and hence compared to a base, seat, foundation or the like of an object. The function of the stepped base dielectric material lies in that the measurement counter electrode is disposed so as to have the stepped portion with respect to the planar inter-electrode dielectric material (raised from the planar inter-electrode dielectric material). The particulate matter is collected by the electric discharge of the second electrode, which takes place on the surface of the inter-electrode dielectric material including the surfaces of the stepped base dielectric material and measurement counter electrode.

The third particulate matter detection device according to the present invention preferably further comprises a flow rate meter which measures or estimates the flow rate of the gas flowing through the space; and particulate matter concentration calculation means for calculating the concentration of the particulate matter in the gas flowing through the space based on the flow rate of the gas measured or estimated by the flow rate meter and the amount of the particulate matter.

In the third particulate matter detection device according to the present invention, the electric characteristics are preferably one or more electric characteristics selected from the electric characteristic group consisting of a resistance, an inductance, a capacitance and an impedance.

In the third particulate matter detection device according to the present invention, the measurement counter electrode preferably has a linear shape, and is disposed so as to be long in a direction vertical to a direction in which the gas including the particulate matter flows. In this case, the measurement counter electrode having the linear shape is preferably disposed over the whole surface of the planar dielectric material (the inter-electrode dielectric material) while bending.

In the third particulate matter detection device according to the present invention, the second electrode preferably has a plate-like shape. In this case, the second electrode is preferably constituted of a tubular wall surface. That is, the second electrode is formed into a tubular shape constituted of a curved surface by rounding a plate-like material, and specifically corresponds to the whole surface or one surface of an exhaust tube.

In the third particulate matter detection device according to the present invention, the second electrode preferably has a needle-like or rod-like shape.

The third particulate matter detection device according to the present invention preferably further comprises a dielectric material (an off-electrode dielectric material) which covers the other surface of the first electrode having the plate-like shape; and a heater disposed on the surface of the dielectric material (the off-electrode dielectric material).

The third particulate matter detection device according to the present invention preferably further comprises a power source for removal which applies a voltage between the first electrode and the measurement counter electrode to oxidize and remove the particulate matter by the discharge of electricity along the surface, wherein the voltage is applied to perform the discharge of the electricity along the surface of the planar dielectric material (the inter-electrode dielectric material) which covers the one surface of the first electrode.

In the third particulate matter detection device according to the present invention, the measurement counter electrode is preferably covered with a film-like dielectric material.

The first particulate matter detection device according to the present invention is a device installed in a through channel through which the gas (the exhaust gas) including the particulate matter passes, to detect the particulate matter included in the gas. In the first particulate matter detection device according to the present invention, the power source for dust collection applies the voltage to the second electrode, thereby allowing the electrode to perform the discharge of the electricity, whereby the particulate matter included in the gas flowing through the space between the first electrode on the side of the inter-electrode dielectric material and the second electrode is electrically charged, or the pre-charged particulate matter is collected by the surface of the inter-electrode dielectric material which covers the first electrode. In this case, the particulate matter is deposited on the inter-electrode dielectric material, and the electric characteristics between the pair of measurement electrodes disposed on the surface of the inter-electrode dielectric material change while keeping a constant relation between the electric characteristics and the amount of the deposited particulate matter. Therefore, the first particulate matter detection device according to the present invention, the change amount of the electric characteristics is acquired, to obtain the amount of the particulate matter collected by the surface of the inter-electrode dielectric material. Since quantification is enabled, it is naturally possible to judge the presence/absence of the particulate matter in the gas flowing through the space (whether or not the amount is zero (0)). Therefore, the first particulate matter detection device according to the present invention is referred to as the detection device. In the first particulate matter detection device according to the present invention, the amount of the particulate matter included in the gas flowing through the space is corrected and obtained based on the amount of the particulate matter, and the concentration of the particulate matter in the gas can be calculated from a relation between the amount and the flow rate of the gas flowing through the space.

In the first particulate matter detection device according to the present invention, to detect, for example, the change amount of the impedance as one of the electric characteristics, the change of a current at the level of 10 nanoamperes (nA) may be measured, depending on the sizes of a measured frequency and a measured voltage. Therefore, the first particulate matter detection device according to the present invention does not become expensive, can easily perform the detection of the particulate matter or the measurement of the amount of the particulate matter and further the measurement of the concentration thereof, and has an only small measurement error. In addition, the generation of the defect of a diesel engine or the like or the defect of a DPF can immediately be detected by the detection of the particulate matter, the measurement of the amount of the particulate matter and the measurement of the concentration thereof, so that the first particulate matter detection device according to the present invention contributes to the decrease of the amount of the discharged particulate matter and the prevention of the air pollution.

In the first particulate matter detection device according to the present invention, the measurement electrodes for measurement the electric characteristics is present on the surface of the same dielectric material. Therefore, the degree of freedom in setting a distance between the measurement electrodes is high, a high sensitivity can easily be obtained, and an arbitrary sensitivity can be obtained in accordance with an application.

In the first particulate matter detection device according to the present invention, there are separately and independently provided a system of the first electrode for charging and collecting the particulate matter, the second electrode and the power source for dust collection; a system of the pair of measurement electrodes for measuring the electric characteristics which change in accordance with the amount of the particulate matter deposited on the inter-electrode dielectric material, the characteristic measurement means and the particulate matter amount calculation means; and the flow rate meter. Therefore, the device includes a control unit which includes input/output means of electric signals from these systems and which controls the whole device, whereby the particulate matter is detected in a dynamic state in which air flows through the space, and the constantly changing amount of the particulate matter and the concentration can be measured in real time.

In a preferable configuration of the first particulate matter detection device according to the present invention, the pair of measurement electrodes have the linear shape and are disposed on the surface of the inter-electrode dielectric material so as to be long in the direction vertical to the direction in which the gas including the particulate matter flows and so as to face each other. Furthermore, each of the pair of measurement electrodes having the linear shape is branched into a plurality of electrodes, and has a plurality of facing portions. In addition, the pair of measurement electrodes having the plurality of facing portions are disposed over the whole surface of the inter-electrode dielectric material. In the first particulate matter detection device according to the present invention, the measurement sensitivity of the electric characteristics can be improved, the particulate matter deposited on the inter-electrode dielectric material can be detected without being missed, and the device has a high accuracy in measuring the amount and concentration of the particulate matter.

In the preferable configuration of the first particulate matter detection device according to the present invention, especially in a case where the second electrode has the plate-like shape, it is possible to employ a configuration in which the second electrode is constituted of the tubular wall surface, and hence the device can compactly be received in the exhaust tube of the diesel engine or the like.

The preferable configuration of the first particulate matter detection device according to the present invention includes the heater disposed on the surface of the off-electrode dielectric material, and hence the electric characteristics measured by the measurement electrodes are stabilized. In addition, the particulate matter can be oxidized and removed by the heat of the heater, and hence the particulate matter can repeatedly accurately be detected.

The preferable configuration of the first particulate matter detection device according to the present invention includes the power source for removal which applies the voltage between the first electrode and the pair of measurement electrodes, and the voltage can be applied to perform the discharge of the electricity along the surface of the inter-electrode dielectric material which covers the one surface of the first electrode, whereby the particulate matter collected by the discharge of the electricity along the surface can be oxidized and removed. By this oxidation removal, the particulate matter can repeatedly and accurately be detected.

In the preferable configuration of the first particulate matter detection device according to the present invention, since the measurement electrodes are covered with the film-like dielectric material, deterioration due to the electric discharge or the exhaust gas does not easily occur.

The preferable configuration of the first particulate matter detection device according to the present invention includes the detection device main body constituted of the dielectric material provided with the through hole as the space through which the gas including the particulate matter flows, the dielectric material being long in one direction. The first electrode and the second electrode are embedded in the detection device main body so as to sandwich the through hole therebetween while the one surface of the first electrode faces the side of the through hole, and the pair of measurement electrodes are disposed on the inner wall surface of the through hole in which the first electrode is embedded. According to the first particulate matter detection device of the present invention of such a configuration, an only portion including the through hole, the first electrode and the second electrode is inserted into a pipe through which a high-temperature exhaust gas circulates, and the other end of the main body can be protruded externally from the pipe. In consequence, portions which are preferably not exposed to the high temperature, for example, the first electrode, the second electrode, the takeoff terminal of the pair of measurement electrodes and the like can be protruded externally from the pipe, and the particulate matter can accurately and stably be detected.

In the preferable configuration of the first particulate matter detection device according to the present invention, the other end of the detection device main body is provided with the takeoff terminal of at least one of the first electrode and the second electrode. According to the first particulate matter detection device of the present invention of such a configuration, the takeoff terminal disposed on the other end of the detection device main body can be protruded externally from the pipe, and the particulate matter can accurately and stably be detected.

In the preferable configuration of the first particulate matter detection device according to the present invention, at least one heater is embedded in the position of at least one of the first electrode and the second electrode on the side opposite to the side on which the through hole is formed. According to the first particulate matter detection device of the present invention of such a configuration, the electric characteristics measured by the measurement electrodes are stabilized. In addition, since the particulate matter can be oxidized and removed by the heat of the heater, the particulate matter can repeatedly accurately be detected.

The second particulate matter detection device according to the present invention is a device installed in the through channel through which the gas (the exhaust gas) including the particulate matter passes, to detect the particulate matter included in the gas. In the second particulate matter detection device according to the present invention, the power source applies the voltage to the second electrode, thereby allowing the electrode to perform the discharge of the electricity, whereby the particulate matter included in the gas flowing through the space between the first electrode on the side of the inter-electrode dielectric material and the second electrode is charged, or the pre-charged particulate matter is collected by the surface of the inter-electrode dielectric material which covers the first electrode. In this case, the particulate matter is deposited on the inter-electrode dielectric material, and the electric characteristics between the first electrode and the measurement counter electrode provided to sandwich therebetween the inter-electrode dielectric material with the particulate matter deposited thereon change while keeping a constant relation between the electric characteristics and the amount of the deposited particulate matter. Therefore, in the second particulate matter detection device according to the present invention, the change amount of the electric characteristics is acquired, to obtain the amount of the particulate matter collected by the surface of the inter-electrode dielectric material. Since quantification is enabled, it is naturally possible to judge the presence/absence of the particulate matter in the gas flowing through the space (whether or not the amount is zero (0)). Therefore, the second particulate matter detection device according to the present invention is referred to as the detection device. In the second particulate matter detection device according to the present invention, the amount of the particulate matter included in the gas flowing through the space is corrected and obtained based on the amount of the particulate matter, and the concentration of the particulate matter in the gas can be calculated from a relation between the amount and the flow rate of the gas flowing through the space.

In the second particulate matter detection device according to the present invention, to detect, for example, the change amount of the impedance as one of the electric characteristics, the change of a current at the level of 10 nanoamperes (nA) may be measured, depending on the sizes of a measured frequency and a measured voltage. Therefore, the second particulate matter detection device according to the present invention does not become expensive, can easily perform the detection of the particulate matter or the measurement of the amount of the particulate matter and further the measurement of the concentration thereof, and has an only small measurement error. In addition, the generation of the defect of a diesel engine or the like or the defect of a DPF can immediately be detected by the detection of the particulate matter, the measurement of the amount of the particulate matter and the measurement of the concentration thereof, so that the second particulate matter detection device according to the present invention contributes to the decrease of the amount of the discharged particulate matter and the prevention of the air pollution.

In the second particulate matter detection device according to the present invention, the electric characteristics change in accordance with the area of the particulate matter deposited on the surface of the measurement counter electrode, whereby even when the physical properties of the particulate matter change, the electric characteristics are not easily influenced by the change of the physical properties.

In a preferable configuration of the second particulate matter detection device according to the present invention, the measurement counter electrode has a plurality of linear portions, and the plurality of linear portions are disposed on the surface of the dielectric material so as to be long in parallel with the direction vertical to the direction in which the gas including the particulate matter flows. Furthermore, the measurement counter electrode having the plurality of linear portions has the lattice-like shape. In addition, the measurement counter electrode having the plurality of linear portions is disposed over the whole surface of the dielectric material. According to the second particulate matter detection device of the present invention of such a configuration, the measurement sensitivity of the electric characteristics can be improved, the particulate matter deposited on the inter-electrode dielectric material can be detected without being missed, and the device has a high accuracy in measuring the amount and concentration of the particulate matter.

In the preferable configuration of the second particulate matter detection device according to the present invention, especially in a case where the second electrode has the plate-like shape, it is possible to employ a configuration in which the second electrode is constituted of the tubular wall surface, and hence the device can compactly be received in the exhaust tube of the diesel engine or the like.

The preferable configuration of the second particulate matter detection device according to the present invention includes the heater disposed on the surface of the off-electrode dielectric material, and hence the electric characteristics measured by the first electrode and the measurement counter electrode are stabilized. In addition, the particulate matter can be oxidized and removed by the heat of the heater, and hence the particulate matter can repeatedly accurately be detected.

The preferable configuration of the second particulate matter detection device according to the present invention includes the power source for removal which applies the voltage between the first electrode and the measurement counter electrode to oxidize and remove the particulate matter by the discharge of the electricity along the surface, and the voltage can be applied to perform the discharge of the electricity along the surface of the inter-electrode dielectric material which covers the one surface of the first electrode, whereby the particulate matter collected by the discharge of the electricity along the surface can be oxidized and removed. By this oxidation removal, the particulate matter can repeatedly and accurately be detected.

In the preferable configuration of the second particulate matter detection device according to the present invention, since the measurement counter electrode is covered with the film-like dielectric material, deterioration due to the electric discharge or the exhaust gas does not easily occur.

The third particulate matter detection device according to the present invention is a device installed in the through channel through which the gas (the exhaust gas) including the particulate matter passes, to detect the particulate matter included in the gas. In the third particulate matter detection device according to the present invention, the power source applies the voltage to the second electrode, thereby allowing the electrode to perform the discharge of the electricity, whereby the particulate matter included in the gas flowing through the space between the first electrode on the side of the inter-electrode dielectric material and the second electrode is electrically charged, or the pre-charged particulate matter is collected by the surface of the inter-electrode dielectric material which mainly covers the first electrode (including the surfaces of the stepped base dielectric material and the measurement counter electrode). In this case, the electric characteristics are radially generated between the measurement counter electrode raised from the inter-electrode dielectric material by the stepped base dielectric material and the first electrode provided so as to mainly sandwich the inter-electrode dielectric material on which the particulate matter is deposited between the first electrode and the measurement counter electrode, and the electric characteristics change while keeping a constant relation between the electric characteristics and the amount of the deposited particulate matter. Therefore, in the third particulate matter detection device according to the present invention, the change amount of the electric characteristics is acquired, to obtain the amount of the particulate matter collected mainly by the surface of the inter-electrode dielectric material. Since quantification is enabled, it is naturally possible to judge the presence/absence of the particulate matter in the gas flowing through the space (whether or not the amount is zero (0)). Therefore, the third particulate matter detection device according to the present invention is referred to as the detection device. In the third particulate matter detection device according to the present invention, the amount of the particulate matter included in the gas flowing through the space is corrected and obtained based on the amount of the particulate matter, and the concentration of the particulate matter in the gas can be calculated from a relation between the amount and the flow rate of the gas flowing through the space.

In the third particulate matter detection device according to the present invention, to detect, for example, the change amount of the impedance as one of the electric characteristics, the change of a current at the level of 10 nanoamperes (nA) may be measured, depending on the sizes of a measured frequency and a measured voltage. Therefore, the third particulate matter detection device according to the present invention does not become expensive, can easily perform the detection of the particulate matter or the measurement of the amount of the particulate matter and further the measurement of the concentration thereof, and has an only small measurement error. In addition, the generation of the defect of a diesel engine or the like or the defect of a DPF can immediately be detected by the detection of the particulate matter, the measurement of the amount of the particulate matter and the measurement of the concentration thereof, so that the third particulate matter detection device according to the present invention contributes to the decrease of the amount of the discharged particulate matter and the prevention of the air pollution.

In the third particulate matter detection device according to the present invention, the protruding stepped base dielectric material is provided on the surface of the planar inter-electrode dielectric material, a stepped portion is present, and the particulate matter can physically be trapped by the stepped portion, so that the particulate matter can be collected stably with a low voltage.

In a preferable configuration of the third particulate matter detection device according to the present invention, the measurement counter electrode has the linear shape, and is disposed so as to be long in the direction vertical to the direction in which the gas including the particulate matter flows, and the measurement counter electrode is disposed over the whole surface of the planar dielectric material while bending. According to the third particulate matter detection device of the present invention of such a configuration, the measurement sensitivity of the electric characteristics can be improved, the particulate matter deposited mainly on the inter-electrode dielectric material can be detected without being missed, and the device has a high accuracy in measuring the amount and concentration of the particulate matter.

In the preferable configuration of the third particulate matter detection device according to the present invention, especially in a case where the second electrode has the plate-like shape, it is possible to employ a configuration in which the second electrode is constituted of the tubular wall surface, and hence the device can compactly be received in the exhaust tube of the diesel engine or the like.

The preferable configuration of the third particulate matter detection device according to the present invention includes the heater disposed on the surface of the off-electrode dielectric material, and hence the electric characteristics measured by the first electrode and the measurement counter electrode are stabilized. In addition, the particulate matter can be oxidized and removed by the heat of the heater, and hence the particulate matter can repeatedly accurately be detected.

The preferable configuration of the third particulate matter detection device according to the present invention includes the power source for removal which applies the voltage between the first electrode and the measurement counter electrode to oxidize and remove the particulate matter by the discharge of the electricity along the surface, and the voltage can be applied to perform the discharge of the electricity along the surface of the inter-electrode dielectric material which covers the one surface of the first electrode, whereby the particulate matter collected by the discharge of the electricity along the surface can be oxidized and removed. By this oxidation removal, the particulate matter can repeatedly and accurately be detected.

In the preferable configuration of the third particulate matter detection device according to the present invention, since the measurement counter electrode is covered with the film-like dielectric material, deterioration due to the electric discharge or the exhaust gas does not easily occur.

DESCRIPTION OF REFERENCE NUMERALS

Figure 1:
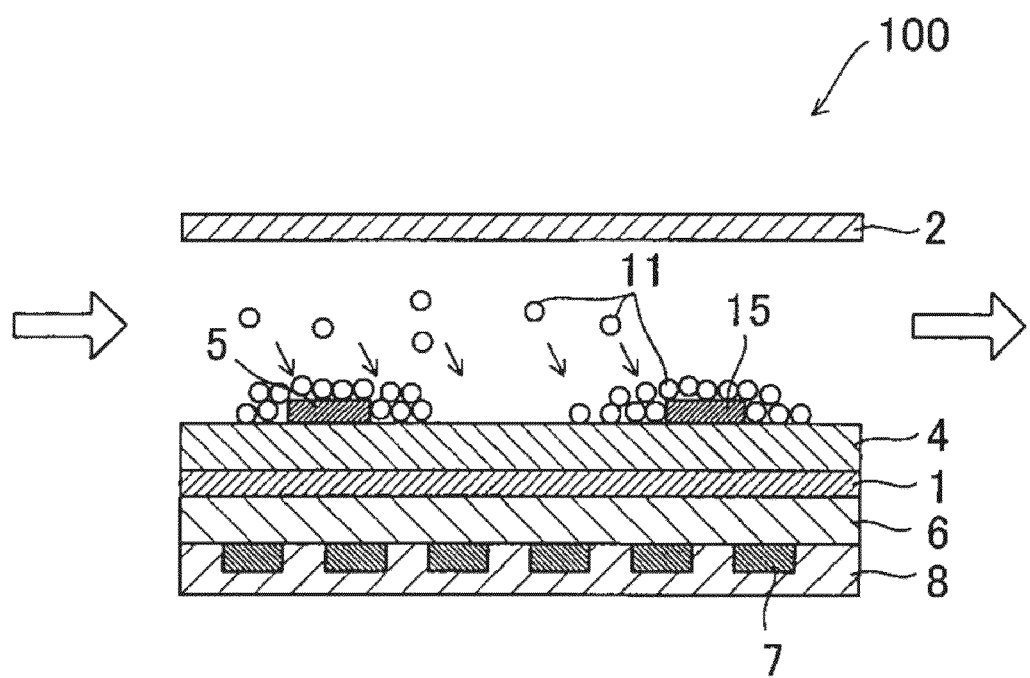
FIG. 1 is a sectional view schematically showing one embodiment of a first particulate matter detection device according to the present invention.

1, 701 and 801: first electrode, 2, 202, 302, 702 and 802: second electrode, 3, 703 and 803: a characteristic measurement unit, 4, 704 and 804: inter-electrode dielectric material, 5, 15, 105, 115, 205 and 215: measurement electrode, 6, 706 and 806: off-electrode dielectric material, 7, 707 and 807: heater, 8, 708 and 808: insulating material, 9: power source for dust collection, 10, 710 and 810: power source for a heater, 11: particulate matter, 12, 712 and 812: control unit, 13, 713 and 813: particulate matter amount calculation unit, 14, 714 and 814: flow rate meter, 16, 716 and 816: particulate matter concentration calculating unit, 21: detection device main body, 21a: one end, 21b: other end, 21c: one tip portion, 21d: other tip portion, 22: through hole, 22a: inlet portion, 22b: enlarged portion, 31: first electrode, 31a, 32a, 33a, 41a and 42a: takeoff terminal, 31b, 32b and 33b: wire, 32: second electrode, 33: heater, 41, 42: measurement electrode, 100, 200, 300, 400, 500, 600, 700, 720, 730, 740, 800, 820 and 830: particulate matter detection unit, 705, 715, 805 and 815: measurement counter electrode, 709, 809: power source, L1: depth of the enlarged portion, L2: length of the through hole in a gas circulating portion, T1: enlarged width, and T2: not-enlarged width.

DETAILED DESCRIPTION OF THE INVENTION

Hereinafter, embodiments of the present invention will be described appropriately with reference to the drawings, but the present invention is not limited to these embodiments when interpreted. The present invention can variously be altered, modified, improved or replaced based on the knowledge of any person skilled in the art without departing from the scope of the present invention. For example, the drawings show preferable embodiments of the present invention, but the present invention is not limited to configurations or information shown in the drawings. To implement or verify the present invention, means similar or equivalent to means described in the present specification is applicable, but preferable means is the following means.

[(1) First Particulate Matter Detection Device] First, a constitution, function, operation and the like of a first particulate matter detection device according to the present invention will mainly be described.

Figure 7:
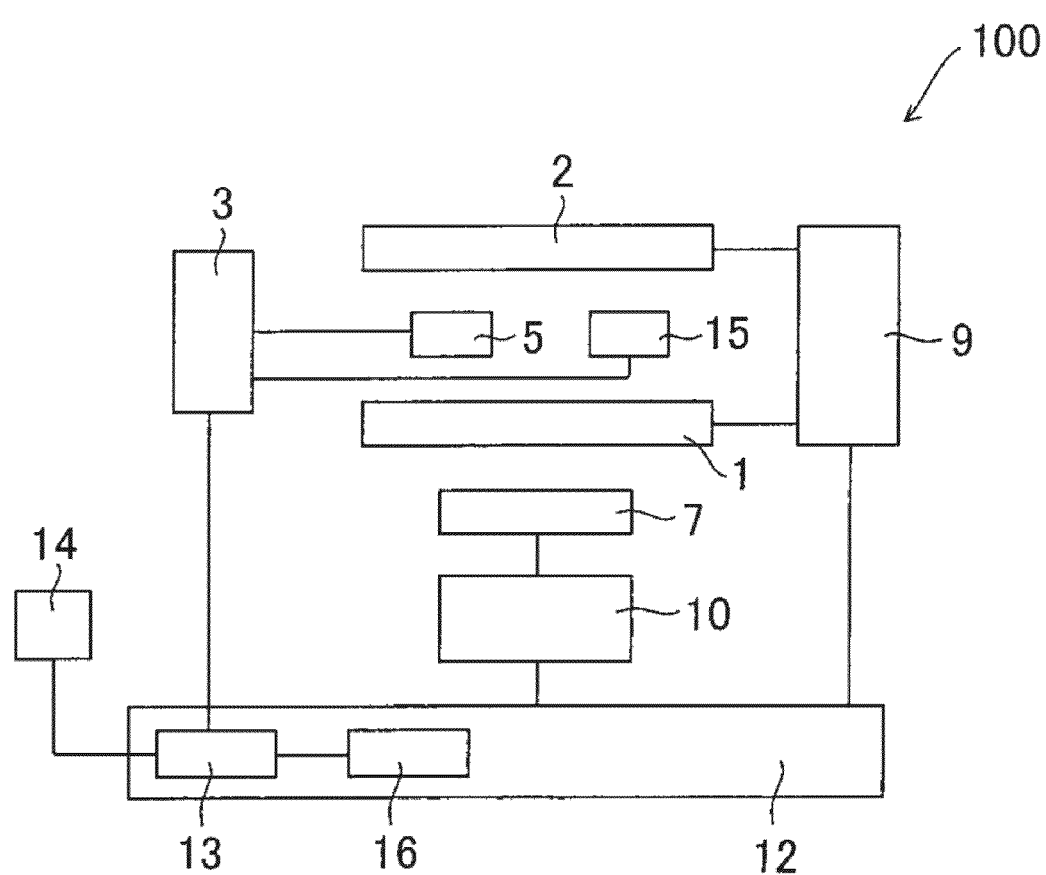
FIG. 7 is a diagram schematically showing the embodiment of the first particulate matter detection device according to the present invention, and is a constitution diagram showing an electric control system.

FIGS. 1 and 7 are diagrams schematically showing one embodiment of the first particulate matter detection device according to the present invention. FIG. 1 is a sectional view, and FIG. 7 is a constitution diagram showing an electric control system. A particulate matter detection device 100 shown in FIGS. 1 and 7 is constituted of a first electrode 1 having a plate-like shape, a second electrode 2 having a plate-like shape, an inter-electrode dielectric material 4 which covers the upper surface (one surface) of the first electrode 1 (in FIG. 1), a power source 9 for dust collection which applies a voltage between the first electrode 1 and the second electrode 2, measurement electrodes 5, 15 having a linear shape and disposed on the surface of the inter-electrode dielectric material 4 so as to face each other, an off-electrode dielectric material 6 which covers the lower surface (the other surface) of the first electrode 1 (in FIG. 1), a heater 7 disposed on the surface (the lower surface in FIG. 1) of the off-electrode dielectric material 6, a power source 10 for the heater which supplies electricity to the heater 7, a sheet-like insulating material 8 which covers, protects and insulates the heater 7 from a portion around the heater, a characteristic measurement unit (means) 3, a particulate matter amount calculation unit (means) 13 which calculates the amount of a particulate matter 11, a particulate matter concentration calculating unit (means) 16 which calculates the concentration of the particulate matter 11, a flow rate meter 14 and a control unit 12. It is to be noted that a portion constituted of the first electrode 1, the second electrode 2, the inter-electrode dielectric material 4, the measurement electrodes 5, 15, the off-electrode dielectric material 6, the heater 7 and the insulating material 8 shown in FIG. 1 is installed in a through channel through which an exhaust gas including the particulate matter 11 passes. They are referred to a sensor portion sometimes.

In the particulate matter detection device 100, the exhaust gas including the particulate matter 11 flows from the left to the right through a space between the inter-electrode dielectric material 4 which covers the first electrode 1 having the plate-like shape and the second electrode 2 having the plate-like shape as shown (by arrows) in FIG. 1. The flow rate of this exhaust gas is measured by the flow rate meter 14 which is not shown in FIG. 1. In this state, when the power source 9 for dust collection applies, for example, a direct-current high voltage to the second electrode 2, electric discharge occurs, the exhaust gas (molecules) around the second electrode 2 is separated into positively charged ions and negatively charged ions, and the negatively charged ions move toward the first electrode 1 to which a positive direct-current high voltage has been applied. At this time, the particulate matter 11 included in the exhaust gas collides with the negatively charged ions, and is negatively charged. Then, the charged particulate matter 11 is collected and deposited on the surface of the inter-electrode dielectric material 4 which covers the positive first electrode 1, by an electrostatic force. In this case, (for example) the electric characteristics between the pair of measurement electrodes 5 and 15 change in accordance with the degree of the deposition of the particulate matter 11. Therefore, when the change amount of the electric characteristics is acquired, the amount of the particulate matter (PM) collected and deposited on the surface of the inter-electrode dielectric material 4 is obtained. Then, the concentration of the PM in the exhaust gas is obtained from the amount of the deposited PM.

Figure 8:
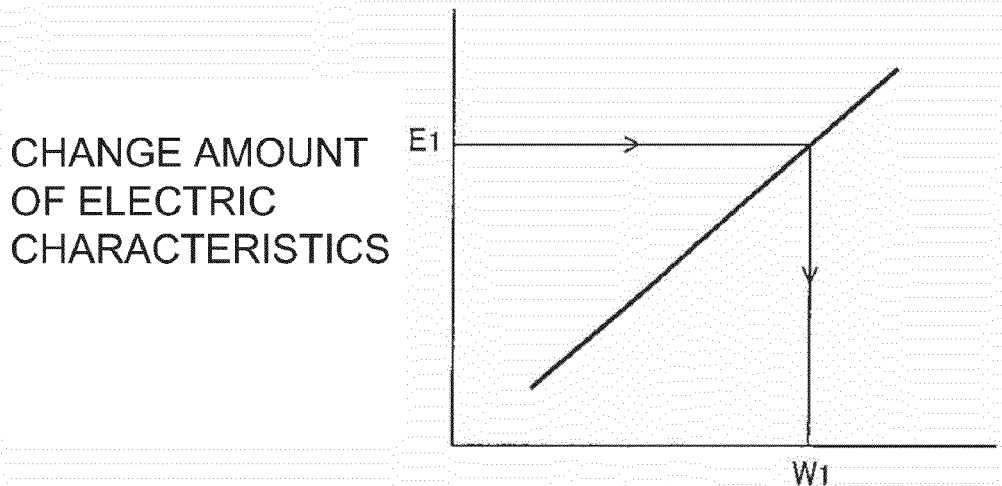
FIG. 8 is a graph for explaining the function of a particulate matter amount calculation unit in the particulate matter detection device according to the present invention.
Figure 9:
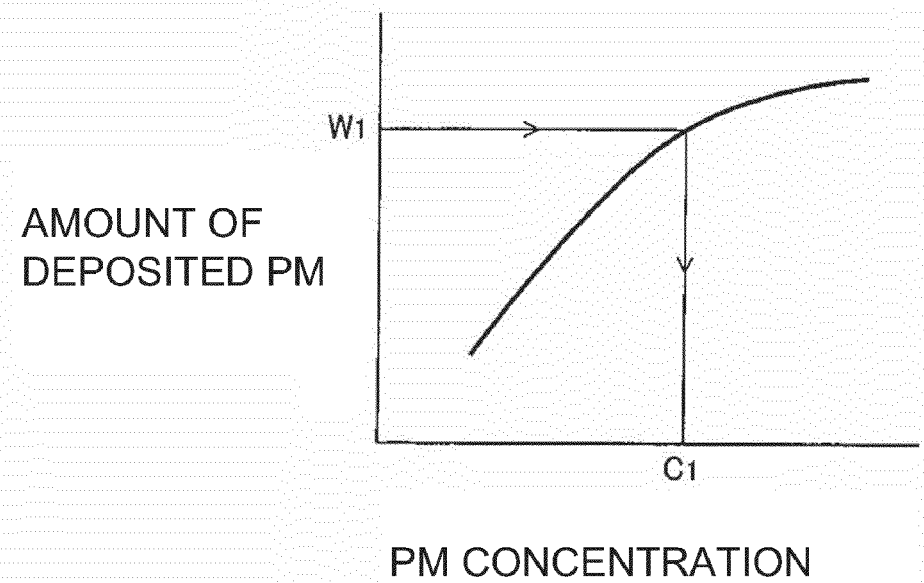
FIG. 9 is a graph for explaining the function of a particulate matter concentration calculating unit in the particulate matter detection device according to the present invention.

FIG. 8 is a graph for explaining the function of the particulate matter amount calculation unit 13, and FIG. 9 is a graph for explaining the function of the particulate matter concentration calculating unit 16. A change amount E1 of the electric characteristics between the measurement electrodes 5 and 15 has a constant relation between the change amount and an amount W1 of the deposited PM (see FIG. 8). Therefore, when the characteristic measurement unit 3 acquires the change amount E1 of the electric characteristics, the particulate matter amount calculation unit 13 having a calculating function based on FIG. 8 obtains the amount W1 of the deposited PM. Moreover, when the flow rate of the exhaust gas is set to a constant rate, the amount W1 of the deposited PM has a constant relation between the amount and a PM concentration C1 (see FIG. 9). When the amount W1 of the deposited PM is acquired, the particulate matter concentration calculating unit 16 having a calculating function based on FIG. 9 obtains the PM concentration C1. When the flow rate of the exhaust gas changes, the particulate matter concentration calculating unit 16 corrects the flow rate based on the flow rate obtained by the flow rate meter 14, to obtain the PM concentration C1 from the amount W1 of the deposited PM.

In the particulate matter detection device 100, the particulate matter concentration calculating unit 16 is incorporated in the control unit 12. The control unit 12 is constituted of, for example, a sequencer having an electric signal input/output function or the like, and includes, in addition to the particulate matter concentration calculating unit 16, a function of inputting the electric signal of the flow rate measured by the flow rate meter 14, to control the power source 10 for the heater or the power source 9 for dust collection and to control the whole device including the switching of a measurement mode and the like.

When, for example, the impedance is obtained as one of the electric characteristics between the measurement electrodes 5 and 15, an alternating-current power source is used, whereby a resistance, a capacitance and an inductance can be measured, respectively. Alternatively, the change of the voltage between the measurement electrodes 5 and 15 may be measured by using a direct-current source, to measure the change of the impedance. The change of the current flowing between the measurement electrodes 5 and 15 or the change of an electric charge accumulated between the measurement electrodes 5 and 15 may be measured by using a direct-current voltage source, to measure the change of the impedance between the measurement electrodes 5 and 15. The characteristic measurement unit 3 can have an appropriate constitution in accordance with a way of obtaining such electric characteristics and the change of the characteristics.

The characteristic measurement unit 3 may be constituted of, for example, an alternating-current power source for applying the voltage to the measurement electrodes 5, 15 and a measurement unit. Examples of the measurement unit preferably include an LCR meter.

As described above, the first particulate matter detection device according to the present invention can detect the particulate matter and measure the amount and concentration of the particulate matter in a static state in which any air does not flow through the space. Alternatively, the detection device can detect the particulate matter, measure the constantly changeable amount of the particulate matter and measure the concentration of the particulate matter in real time in a dynamic state in which the air flows through the space. However, a dust collection efficiency varies in accordance with the flow rate of charged particles. Therefore, as to grounds for obtaining the amount W1 of the deposited PM from the change amount E1 of the electric characteristics in the particulate matter amount calculation unit 13 (corresponding to data shown in FIG. 8) and grounds for obtaining the PM concentration C1 from the amount W1 of the deposited PM in the particulate matter concentration calculating unit 16 (corresponding to data shown in FIG. 9), the former and the latter need to use different grounds (data) in separate measurement modes.

A distance between the inter-electrode dielectric material 4 and the second electrode 2 forming the exhaust gas flowing space is preferably 0.5 to 50 mm, more preferably 0.6 to 40 mm. When the distance is set to such a range, the electricity can more efficiently be discharged, and the particulate matter can more efficiently be collected. When the distance between the inter-electrode dielectric material 4 and the second electrode 2 is shorter than 0.5 mm, a dust collection ratio decreases, and a measurement accuracy deteriorates sometimes. When the distance is longer than 50 mm, a higher voltage is necessary, and energy is wasted sometimes.

The power source 9 for dust collection supplies a stable direct-current voltage or alternating-current voltage between the first electrode 1 and the second electrode 2 so that the electric discharge can be caused. As the power source 9 for dust collection, for example, a power source using a power source circuit by a flyback system or the like may be employed. In this case, the energy is accumulated from an input-side power source to a transformer, and the accumulated energy can be discharged to an output side to supply a high direct-current voltage. In the power source circuit by the flyback system, the accumulation and discharge of the energy in and from the transformer are controlled by a transistor or the like, and an output-side current is rectified by a diode.

Figure 4:
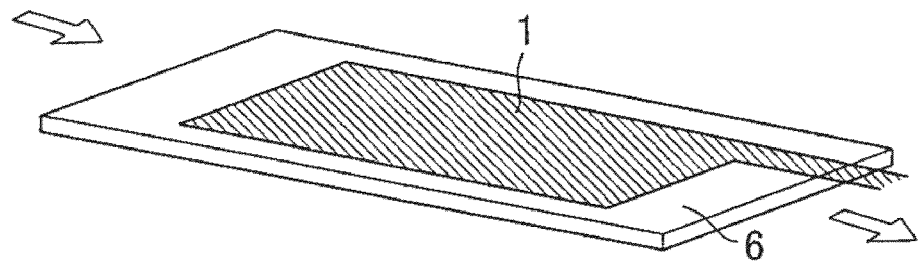
FIG. 4 is a diagram schematically showing the embodiment of the first particulate matter detection device according to the present invention, and is a perspective view showing an off-electrode dielectric material and a first electrode.

FIG. 4 is a perspective view showing the off-electrode dielectric material 6 and the first electrode 1. In FIG. 4, arrows show the flow direction of the exhaust gas. The first electrode 1 discharges the electricity as a counter electrode of the second electrode 2, and performs a function of a member for sucking and collecting the charged particulate matter 11. As shown in FIG. 4, the plate-like first electrode 1 in the particulate matter detection device 100 has a substantially rectangular shape, but examples of the shape that can be employed include a polygonal shape such as a pentangular shape, a circular shape, an elliptic shape, a track shape, a shape having unevenness in the outer periphery thereof and a shape including one or a plurality of slits.

The plate-like second electrode 2 is not shown in a perspective view, but has a substantially rectangular shape in the same manner as in the first electrode 1. In the same manner as in the first electrode 1, examples of the shape of the second electrode that can be employed include a polygonal shape such as a pentangular shape, a circular shape, an elliptic shape, a track shape, a shape having unevenness in the outer periphery thereof and a shape including one or a plurality of slits.

The linear measurement electrodes 5, 15 are disposed so as to be long in a direction vertical to the direction in which the exhaust gas flows (arrows in FIG. 1) and so that the measurement electrodes 5, 15 face each other, whereby the change of the electric characteristics between the measurement electrodes 5 and 15 is measured. The distance between the measurement electrode 5 and the measurement electrode 15 is set to a range in which it is possible to clearly measure the change of the electric characteristics between the measurement electrodes 5 and 15 generated when collecting the particulate matter 11 by the first electrode 1. The distance is, for example, about 0.2 to 10 mm.

Figure 5:
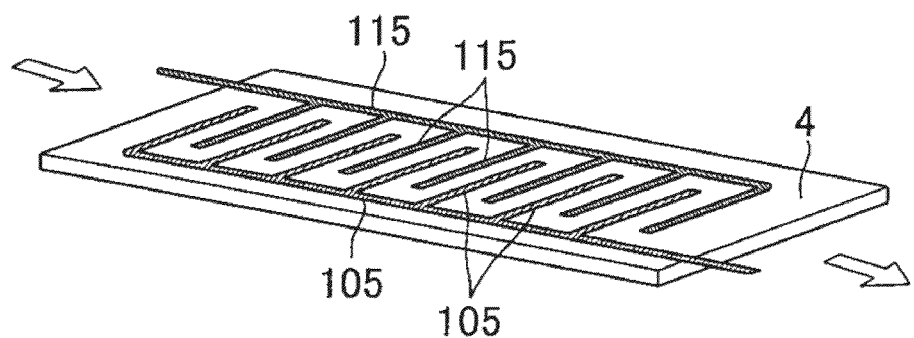
FIG. 5 is a diagram schematically showing the embodiment of the first particulate matter detection device according to the present invention, and is a perspective view showing another configuration of measurement electrodes.
Figure 6:
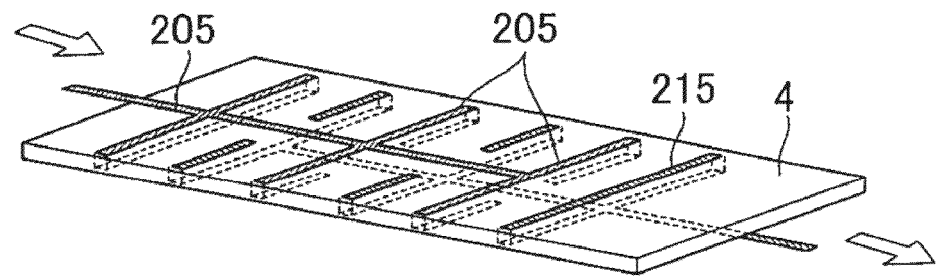
FIG. 6 is a diagram schematically showing the embodiment of the first particulate matter detection device according to the present invention, and is a perspective view showing still another configuration of measurement electrodes.

FIGS. 5 and 6 are perspective views each showing another configuration of a pair of measurement electrodes having a linear shape. In FIGS. 5 and 6, arrows show the flow direction of the exhaust gas. As to measurement electrodes 105, 115 shown in FIG. 5, each of the measurement electrodes 105 and 115 are branched into a plurality of electrodes, the branched measurement electrodes face one another, and a plurality of facing portions are present. In addition, the plurality of facing portions of the branched measurement electrodes 105 and 115 are disposed over the whole surface of the inter-electrode dielectric material 4. In the first particulate matter detection device according to the present invention, from a viewpoint that the measurement sensitivity and measurement accuracy of the electric characteristics be improved, it is not preferable that the distance between a pair of facing measurement electrodes is long. On the other hand, the pair of facing measurement electrodes are preferably disposed at positions corresponding to all of exhaust gas flowing spaces. The measurement electrodes 105, 115 shown in FIG. 5 embody such a preferable configuration. Measurement electrodes 205, 215 shown in FIG. 6 are similar to the above measurement electrodes, but have a different branch configuration. The measurement electrode 205, 215 are each branched into a plurality of electrodes, the branched electrodes face each other, a plurality of facing portions are present, and the plurality of facing portions of the branched measurement electrode 205 and 215 are disposed over the whole surface of the inter-electrode dielectric material 4.

Turning back to the description of the particulate matter detection device 100. The shape and size of the heater 7 may be determined so that all of the particulate matter 11 collected by the surface of the inter-electrode dielectric material 4 can be burnt.

The heater 7 is used not only when the particulate matter 11 is oxidized and removed but also when the change of the electric characteristics between the measurement electrodes 5 and 15 is measured, so that the heater is not influenced by water of dew condensation or the like. For example, when the measurement electrodes 5, 15 are appropriately heated during the detection of the impedance change or the electric discharge, the water can be prevented from being attached to the measurement electrodes 5, 15. At this time, a heating temperature is preferably 200 to 300° C.

From a viewpoint that efficient temperature control can be performed, examples of the power source 10 for the heater preferably include a power source of a step-down chopper system. The power source is especially preferably a switching power source of the step-down chopper system using a self-arc-suppressing type semiconductor switch. In this case, a switching frequency is preferably an audio frequency of 20 kHz or more. Fuel consumption is directly influenced, and hence the current or power of the power source for the heater is preferably set to a smaller value. Moreover, the power source 10 for the heater preferably has a temperature control function of calculating the temperature of the heater 7 from the voltage and the current.

The insulating material 8 suppresses the release of the heat generated by the heater 7, whereby the heat of the heater 7 can efficiently be used for efficiently burning the particulate matter 11. The thickness of the insulating material 8 is preferably such a thickness as to suppress the release of the heat, for example, about 100 to 1000 μm.

It is to be noted that in the particulate matter detection device 100, instead of or together with the heater 7 and the power source 10 for the heater, it is possible to employ a power source for removal which applies a voltage between the first electrode 1 and the pair of measurement electrodes 5, 15 to perform the discharge of the electricity along the surface of the inter-electrode dielectric material 4. In this case, it is necessary to construct a switch circuit in which the measurement electrodes 5, 15 are separated from the characteristic measurement unit 3, and the first electrode 1 is separated from the power source 9 for dust collection, respectively, the measurement electrode 5 and the measurement electrode 15 are energized, and the electrodes and the first electrode 1 are connected to the power source for removal. As the power source for removal, an alternating-current power source or a pulse power source may be employed.

Figure 2:
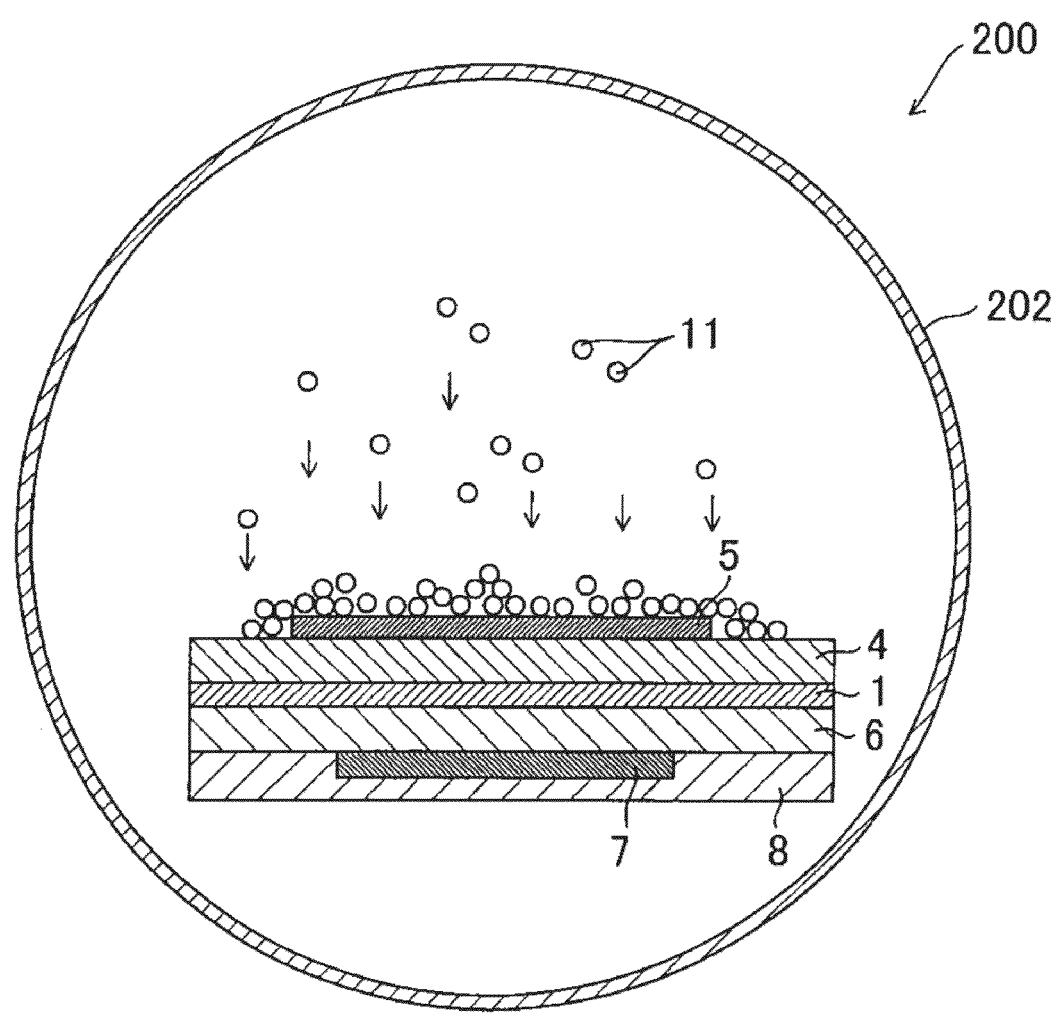
FIG. 2 is a sectional view schematically showing another embodiment of the first particulate matter detection device according to the present invention.
Figure 3:
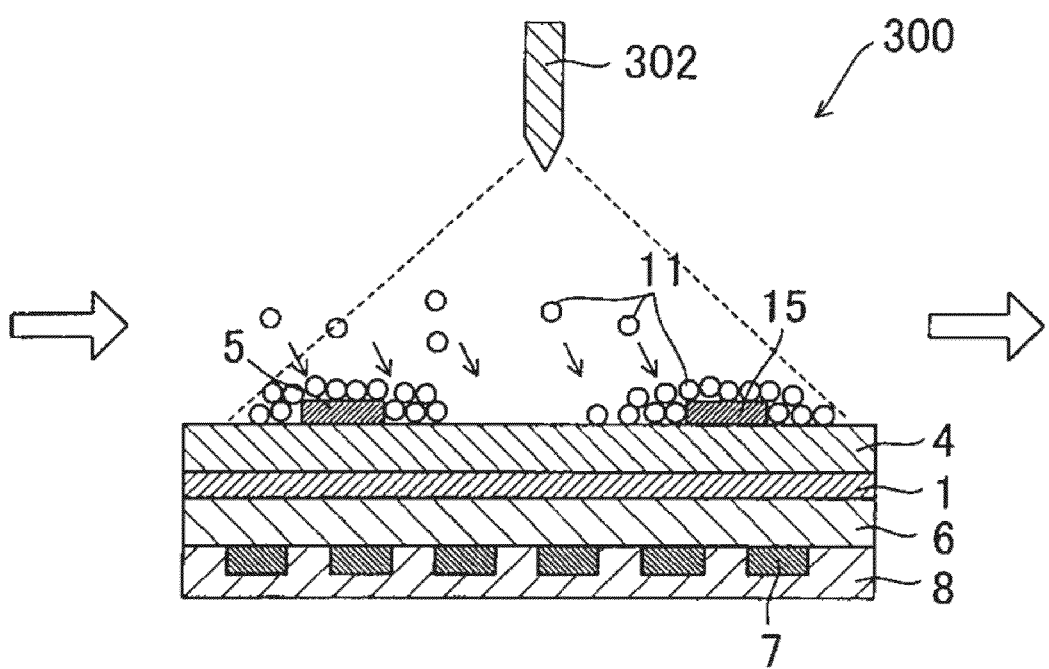
FIG. 3 is a sectional view schematically showing still another embodiment of the first particulate matter detection device according to the present invention.

The embodiment of the first particulate matter detection device according to the present invention has been described above, but examples of another embodiment include an embodiment in which the second electrode is constituted of a tubular wall surface and an embodiment in which the second electrode having a needle-like or rod-like shape is employed. FIG. 2 is a sectional view showing a particulate matter detection device 200 corresponding to the former embodiment. In FIG. 2, the shown direction in which the exhaust gas flows is a direction from the front to the backside. FIG. 3 is a sectional view showing a particulate matter detection device 300 corresponding to the latter embodiment. In the particulate matter detection device 300, corona discharge is performed as electric discharge. In the particulate matter detection devices 200, 300, a device constitution excluding a principle, a function and a second electrode conforms to that of the particulate matter detection device 100, and hence the description thereof is omitted.

Figure 10A:
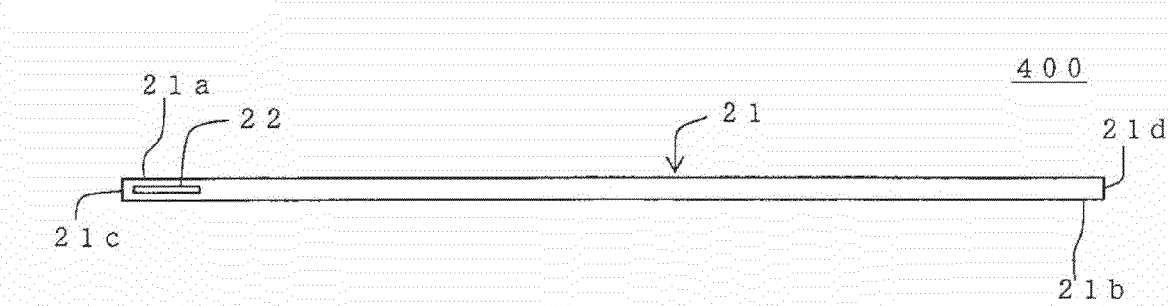
FIG. 10A is a front view schematically showing a further embodiment of the first particulate matter detection device according to the present invention.
Figure 10B:
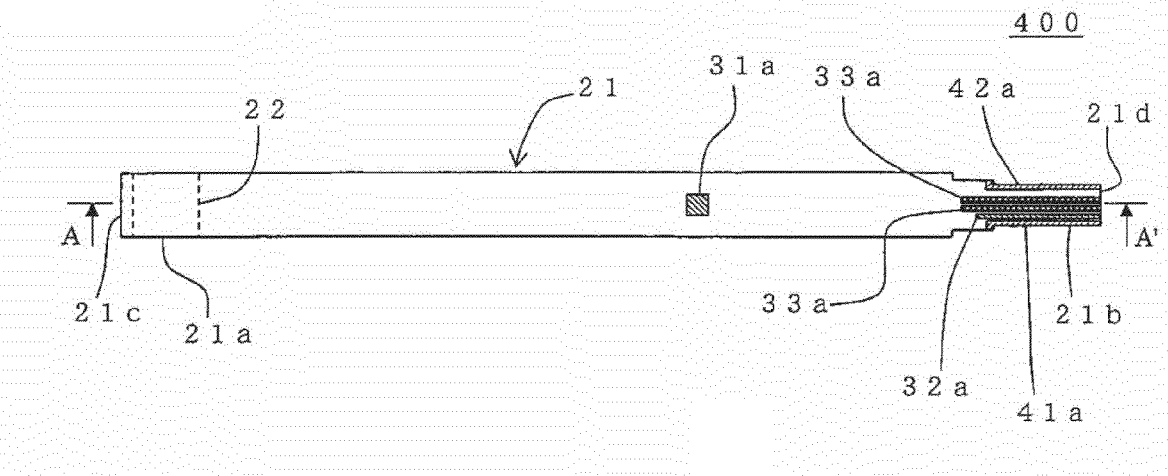
FIG. 10B is a side view schematically showing the embodiment of the first particulate matter detection device according to the present invention.
Figure 11:
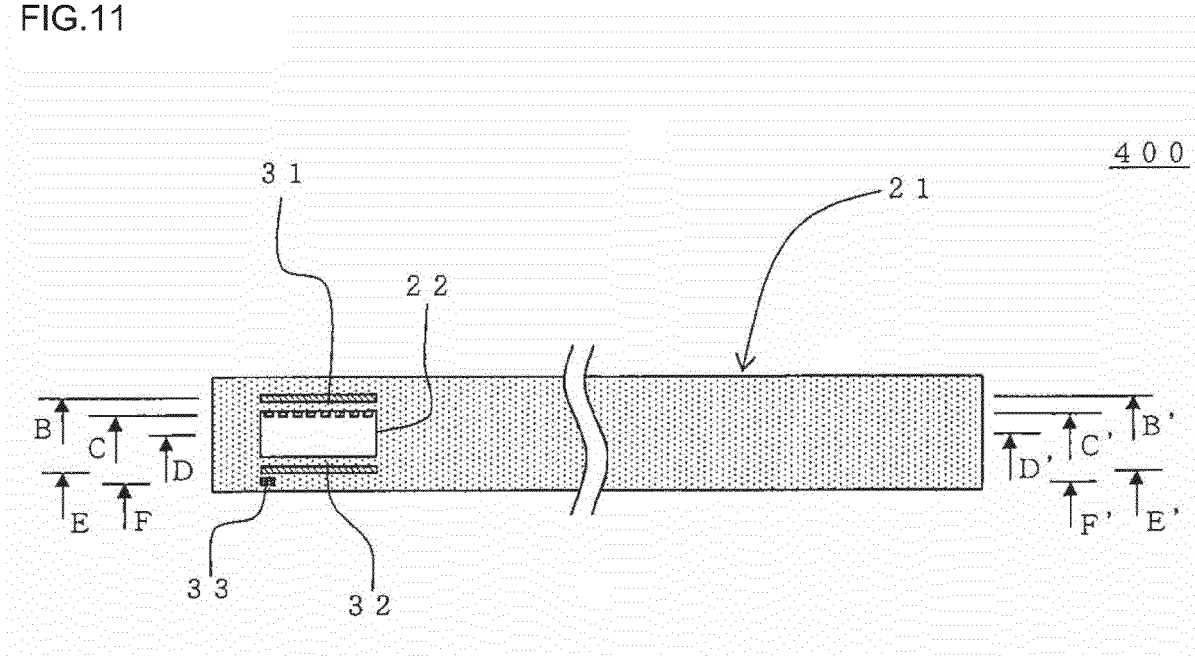
FIG. 11 is a schematic diagram showing a section cut along the A-A' line of FIG. 10B.
Figure 12:
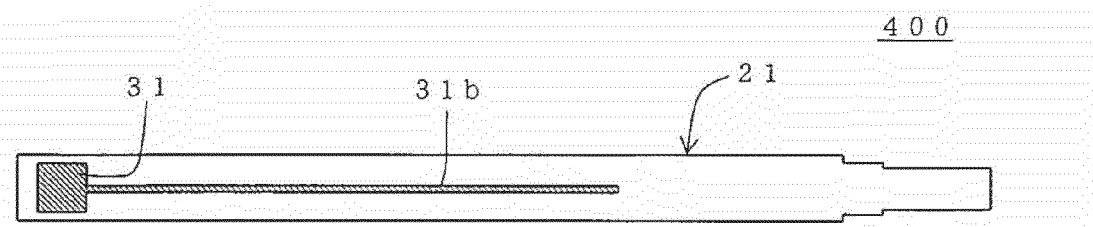
FIG. 12 is a schematic diagram showing a section cut along the B-B' line of FIG. 11.
Figure 13:
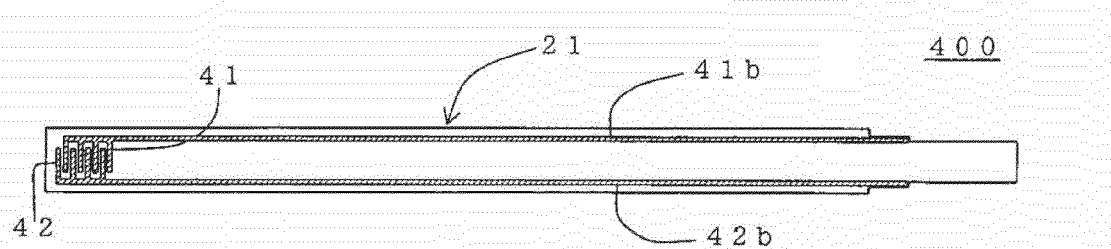
FIG. 13 is a schematic diagram showing a section cut along the C-C' line of FIG. 11.
Figure 14:
FIG. 14 is a schematic diagram showing a section cut along the D-D' line of FIG. 11.
Figure 15:
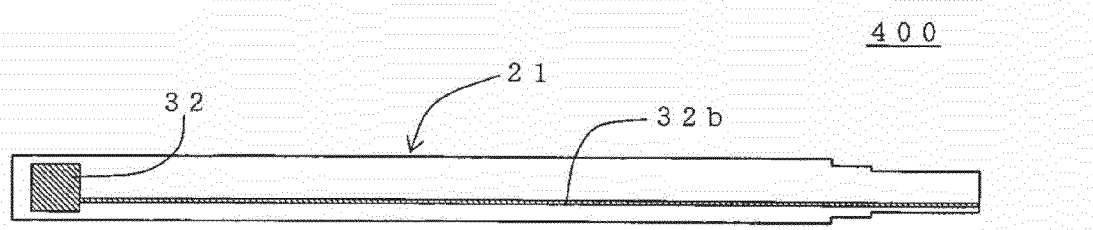
FIG. 15 is a schematic diagram showing a section cut along the E-E' line of FIG. 11.
Figure 16:
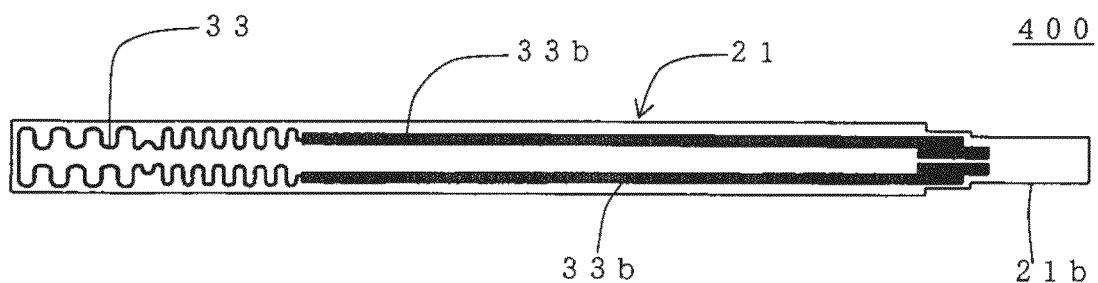
FIG. 16 is a schematic diagram showing a section cut along the F-F' line of FIG. 11.

Next, a further embodiment of the first particulate matter detection device according to the present invention will be described. As shown in FIGS. 10A to 16, a particulate matter detection device 400 includes a detection device main body 21 constituted of a dielectric material provided with, in one end 21*a* thereof, a through hole 22 as a space through which a gas including a particulate matter flows, the dielectric material being long in one direction. A first electrode 31 and a second electrode 32 are embedded in the detection device main body 21 so as to sandwich the through hole 22 therebetween while the one surface of the first electrode 31 faces the side of the through hole 22, and a pair of measurement electrodes 41, 42 are disposed on the inner wall surface of the through hole 22 in which the first electrode 31 is embedded. Here, FIG. 10A is a front view schematically showing the further embodiment of the first particulate matter detection device according to the present invention. FIG. 10B is a side view schematically showing the embodiment of the first particulate matter detection device according to the present invention. FIG. 11 is a schematic diagram showing a section cut along the A-A' line of FIG. 10B. FIG. 12 is a schematic diagram showing a section cut along the B-B' line of FIG. 11. FIG. 13 is a schematic diagram showing a section cut along the C-C' line of FIG. 11. FIG. 14 is a schematic diagram showing a section cut along the D-D' line of FIG. 11. FIG. 15 is a schematic diagram showing a section cut along the E-E' line of FIG. 11. FIG. 16 is a schematic diagram showing a section cut along the F-F' line of FIG. 11.

In the particulate matter detection device 400, the first electrode 31 and the second electrode 32 are embedded in the detection device main body 21, and the detection device main body 21 is formed of the dielectric material, whereby the first electrode 31 and the second electrode 32 are covered with the dielectric material, respectively. That is, the dielectric material which covers the one surface of the first electrode 31 is constituted of a part of the detection device main body 21 than itself if constituted of the dielectric material.

In consequence, it is possible to measure the mass of the particulate matter included in the only exhaust gas that has flowed into the through hole among the exhaust gas flowing through the downstream side of a DPF, and all the particulate matter contained in the exhaust gas flowing through the downstream side of the DPF are not directly measured but the only particulate matter that has flowed into the through hole is measured, whereby the amount of the particulate matter in the whole exhaust gas can be estimated, and hence the particulate matter detection device can be miniaturized. In consequence, the device can be installed in a small space, and can simply inexpensively be manufactured. Moreover, even when the flow rate of the whole exhaust gas flowing through the downstream side of the DPF is a high flow rate, an only part of the exhaust gas (the particulate matter) is introduced into the through hole. Therefore, in a case where electric discharge is caused in the through hole and the particulate matter in the through hole is electrically charged, all the particulate matter in the through hole can effectively electrically be charged, and a measured value with little error can be obtained. Moreover, the detection device main body is formed so as to be long in one direction, the through hole is formed in one end of the main body, and at least a pair of electrodes are disposed (embedded), so that an only portion provided with the through hole and the pair of electrodes is inserted into a pipe through which a high temperature exhaust gas circulates, and the other end of the main body is protruded externally from the pipe. In consequence, a portion which is preferably not exposed to the high temperature, for example, a takeoff terminal of the pair of electrodes or the like can be protruded externally from the pipe, whereby the particulate matter can accurately and stably be detected.

In the particulate matter detection device 400, a takeoff terminal of at least one of the first electrode 31 and the second electrode 32 is preferably disposed in another end 21*b* of the detection device main body 21. The takeoff terminal is a portion which is electrically connected to the electrode disposed in the detection device main body 21 of the particulate matter detection device 400 and which is connected to a wire from a power source for applying a voltage to the electrode from the outside or the like. The particulate matter detection device 400 has a plurality of takeoff terminals (takeoff terminals 31*a*, 32*a*, 33*a*, 41*a* and 42*a*) independently connected to the first electrode 31, the second electrode 32, a heater 33, the measurement electrodes 41, 42 and the like. In the particulate matter detection device 400 shown in FIG. 10B, the takeoff terminal 32*a* of the second electrode 32 is disposed in the other end 21*b* of the detection device main body 21. Thus, the takeoff terminal of at least one of the first electrode 31 and the second electrode 32 is disposed in the other end 21*b* of the detection device main body 21, whereby a large distance can be made between a portion (the one end 21*a*) provided with the through hole 22, the first electrode 31, the second electrode 32 and the pair of measurement electrodes 41, 42 and the takeoff terminal. In consequence, the only one end 21*a* provided with the through hole 22 and the like is inserted into a pipe through which the high temperature exhaust gas circulates, and the other end 21*b* provided with the takeoff terminal 32*a* can be protruded externally from the pipe. When the takeoff terminal 32*a* has a high temperature, the detection accuracy of the particulate matter deteriorates, and stable detection cannot easily be performed sometimes. When the takeoff terminal is used for a long time, a defect is generated in a contact point between the electric terminal and a harness for connection to the outside, and measurement cannot be performed sometimes. Therefore, the takeoff terminal 32*a* is protruded externally from the pipe, and is not exposed to the high temperature, whereby the particulate matter can accurately and stably be detected.

As shown in FIG. 10B, the takeoff terminal 32*a* disposed in the other end 21*b* of the detection device main body 21 is preferably disposed on the side surface of the other end 21*b* of the detection device main body 21 so as to extend in a longitudinal direction. The surface provided with the takeoff terminal 32*a* does not have to be the side surface of the other end 21*b* of the detection device main body 21, and may be any surface. Moreover, in FIG. 10B, the other end 21*b* of the detection device main body 21 is formed with a small width, but the width of the other end 21*b* may be small in this manner or does not have to be small. There is not any special restriction on the shape and size of the takeoff terminal 32*a*. The takeoff terminal preferably has a strip-like shape having a width of 0.1 to 2 mm and a length of 0.5 to 20 mm. Examples of the material of the takeoff terminal 32*a* include Ni, Pt, Cr, W, Mo, Al, Au, Ag, Cu, stainless steel and Kovar.

The takeoff terminals of both the first electrode 31 and the second electrode 32 may be disposed in the other end 21*b* of the detection device main body 21, but the takeoff terminal 32*a* of the second electrode 32 may be disposed in the other end 21*b* of the detection device main body 21 whereas the takeoff terminal 31*a* of the first electrode 31 is preferably disposed at a position between the one end 21a and the other end 21b of the detection device main body 21. In consequence, the takeoff terminal 32a of the second electrode 32 and the takeoff terminal 31a of the first electrode 31 are disposed with a space being left therebetween, whereby when a voltage is applied between the takeoff terminal 31a and the takeoff terminal 32a to apply the voltage between the first electrode 31 and the second electrode 32, short-circuit due to the discharge of electricity along the surface can be prevented from being caused along the surface of the detection device main body 21. Here, "the one end of the detection device main body" is a region from one tip portion 21c of the detection device main body to a position corresponding to a length which is 30% of the total length of the detection device main body 21. Moreover, "the other end of the detection device main body" is a region from another tip portion 21d of the detection device main body to a position corresponding to a length which is 30% of the total length of the detection device main body 21. Therefore, the position between the one end 21a and the other end 21b of the detection device main body 21 is a portion of the detection device main body 21 excluding the regions of the one end 21a and the other end 21b. In the particulate matter detection device 400, a distance between the takeoff terminal 31a and the takeoff terminal 32a is preferably 5 to 100 mm, further preferably 10 to 70 mm. When the distance is shorter than 5 mm, the short-circuit due to the discharge of the electricity along the surface is easily caused sometimes. In a case where the distance is longer than 100 mm and the detection device main body 21 of the particulate matter detection device 400 is attached to the pipe or the like so that the takeoff terminal 31a is positioned outside the pipe, the portion of the detection device main body 21 protruding externally from the pipe becomes excessively long, and it becomes difficult to attach the detection device main body 21 to a small space.

Moreover, a distance between the through hole 22 and the takeoff terminal 31a disposed at the position between the one end 21a and the other end 21b of the detection device main body 21 is preferably longer than 10 mm, further preferably longer than 20 mm. When the distance is shorter than 10 mm and the particulate matter detection device 400 is attached to the pipe so as to insert the portion of the through hole 22 into the pipe, the heat of the high temperature exhaust gas circulating through the pipe easily exerts an influence on the takeoff terminal 31a sometimes.

There is not any special restriction on the shape and size of the takeoff terminal 31a. The shape of the takeoff terminal is, for example, a polygonal shape such as a quadrangular shape having a width of 0.5 to 3 mm and a length of 0.5 to 3 mm, but the terminal may have a circular shape, an elliptic shape, a race track shape or another shape. Examples of the material of the takeoff terminal 31a include Ni, Pt, Cr, W, Mo, Al, Au, Ag, Cu, stainless steel and Kovar.

In the particulate matter detection device 400, the detection device main body 21 is formed so as to be long in one direction, and there is not any special restriction on the length of the main body in the longitudinal direction, but the main body preferably has such a length that the main body can efficiently sample the particulate matter from the exhaust gas when inserted into an exhaust gas pipe. The length of the main body is preferably about 50 to 200 mm. In the particulate matter detection device 400, the through hole 22 is formed in the one end 21a of the main body in the longitudinal direction. Moreover, there is not any special restriction on the thickness of the detection device main body 21 (the length in a direction vertical to both "the longitudinal direction of the detection device main body" and "the circulating direction of the gas" (the thickness direction)), but the thickness is preferably about 0.5 to 3 mm. Here, "the thickness of the detection device main body 21" is the thickness of the thickest portion of the main body in the thickness direction. Moreover, there is not any special restriction on the length of the detection device main body 21 in the circulating direction when the gas circulates through the through hole 22, but the length is preferably about 2 to 20 mm. As shown in FIGS. 10A and 10B, the shape of the detection device main body 21 may be a plate-like shape with a rectangular sectional shape crossing the longitudinal direction at right angles, a rod-like shape with a circular or elliptic sectional shape or the like, and there is not any special restriction on the shape as long as the shape is long in the one direction. Examples of the material of the detection device main body 21 preferably include the suitable materials of the inter-electrode dielectric material 4 and the off-electrode dielectric material 6 in the embodiment of the first particulate matter detection device according to the present invention. Furthermore, cordierite is further preferable because it has an excellent resistance to thermal shock. Any of these materials is the dielectric material, whereby when the first electrode 31 and the second electrode 32 are embedded in the detection device main body 21, the first electrode 31 and the second electrode 32 covered with the dielectric material can be formed. Moreover, the particulate matter detection device 400 has an excellent thermal resistance, resistance to dielectric breakdown or the like. Here, "the dielectric material" is a substance which has dielectric properties rather than conductivity and which behaves as an insulator with respect to the direct-current voltage.

As shown in FIG. 11, in the particulate matter detection device 400, the first electrode 31 and the second electrode 32 are embedded in the wall forming the through hole 22, and the first electrode 31 and the second electrode 32 covered with the dielectric material are disposed so as to sandwich the through hole 22 therebetween. In consequence, when a predetermined voltage is applied between the first electrode 31 and the second electrode 32, the electric discharge can be caused in the through hole 22. It is to be noted that at least a pair of electrodes need to be disposed. Moreover, the electrodes may be embedded in the wall forming the through hole 22, and are preferably disposed so as to sandwich the through hole 22 therebetween as shown in FIG. 11, bit the pair of electrodes may be disposed at any position in the wall surrounding the through hole 22 as long as the electric characteristics of the wall can be detected and the electric discharge can be caused in the through hole 22. The type of the electric discharge is preferably one selected from the group consisting of silent discharge, streamer discharge and corona discharge. To cause such electric discharge, the particulate matter detection device 400 further includes a power source for dust collection connected to the takeoff terminals 31a, 32a. As the power source for dust collection, an alternating-current power source with a high voltage, a direct-current power source or the like is preferable. Moreover, as the voltage to be applied to cause the electric discharge, a pulse voltage, an alternating-current voltage such as a rectangular wave or the like is preferable. Furthermore, as the conditions of the voltage to be applied, 200 kV/cm or more is preferable, depending on a gap or a gas temperature. In addition, when the voltage is applied, a power is preferably 0.1 to 10 W.

In the particulate matter detection device 400, when the particulate matter contained in a fluid flowing into the through hole 22 is not electrically charged, the electric discharge is caused in the through hole 22, whereby the particulate matter is electrically charged and the electrically charged particulate matter is electrically adsorbed by the wall surface of the through hole 22. Moreover, when the particulate matter contained in the fluid flowing into the through hole 22 is already electrically charged before flowing into the through hole 22, the particulate matter does not have to be electrically charged by the electric discharge in the through hole 22, and hence the electrically charged particulate matter is electrically adsorbed by the wall surface of the through hole 22 without causing any electric discharge in the through hole 22. When the electric discharge is caused in the through hole 22 to electrically charge the particulate matter, the electrically charged particulate matter is electrically attracted by the electrode having a polarity opposite to that of the electrically charged particulate matter and is adsorbed by the wall surface during the electric discharge. On the other hand, when the particulate matter is electrically charged before flowing into the through hole 22, the voltage having predetermined conditions is applied between the first electrode 31 and the second electrode 32 so that the particulate matter is electrically attracted by the electrode having the polarity opposite to that of the electrically charged particulate matter. Here, when the particulate matter is electrically charged before flowing into the through hole 22, the conditions of the voltage applied between the first electrode 31 and the second electrode 32 are preferably 4 kV/cm to 40 kV/cm.

There is not any special restriction on the shape and size of each of the first electrode 31 and the second electrode 32 as long as the electric discharge can be caused in the through hole 22. Examples of the shape of the electrode include a rectangular shape, a circular shape and an oblong shape. Moreover, the size of each of the first electrode 31 and the second electrode 32 is preferably 70% or more of the area of the through hole 22 as viewed from the side surface of the through hole.

There is not any special restriction on the thickness of each of the first electrode 31 and the second electrode 32 as long as the electric discharge can be caused in the through hole 22. For example, the thickness is preferably 5 to 30 μm. Examples of the material of the first electrode 31 and the second electrode 32 preferably include the suitable material of the first electrode 31 and the second electrode 32 in the embodiment of the first particulate matter detection device according to the present invention.

A distance between the first electrode 31 and the through hole 22 and a distance between the second electrode 32 and the through hole 22 are preferably 50 to 500 μm, further preferably 100 to 300 μm. In such a range, the electric discharge can effectively be caused in the through hole. The distance between each of the first electrode 31 and the second electrode 32 and the through hole 22 is the thickness of the portion of the dielectric material covering the first electrode 31 or the second electrode 32 and facing the through hole 22.

In the particulate matter detection device 400, as shown in FIG. 12, the first electrode 31 is connected to a wire 31b which extends in the longitudinal direction of the detection device main body 21, and the tip (the tip which is not connected to the first electrode 31) portion of the wire 31b is interlayer-connected to (via connection) the takeoff terminal 31a shown in FIG. 10B. Moreover, as shown in FIG. 13, the measurement electrodes 41 and 42 are connected to wires 41b and 42b extending in the longitudinal direction of the detection device main body 21, respectively, and the tip (the tip which is not connected to the measurement electrode 41 or 42) portion of each of the wires 41b, 42b is interlayer-connected to each of the takeoff terminals 41a, 42a shown in FIG. 10B. Moreover, the takeoff terminals 41a, 42a of the measurement electrodes 41, 42 are connected to the characteristic measurement unit 3 (see FIG. 7). Furthermore, the characteristic measurement unit 3 (see FIG. 7) is connected to the particulate matter amount calculation unit 13 (see FIG. 7). In addition, as shown in FIG. 14, the one end 21a of the detection device main body 21 is provided with the through hole 22. Here, FIG. 12 is a schematic diagram showing a section cut along the B-B' line of FIG. 11, FIG. 13 is a schematic diagram showing a section cut along the C-C' line of FIG. 11, and FIG. 14 is a schematic diagram showing a section cut along the D-D' line of FIG. 11.

Moreover, as shown in FIG. 15, the second electrode 32 is connected to a wire 32b which extends in the longitudinal direction of the detection device main body 21, and the wire 32b is interlayer-connected to the takeoff terminal 32a shown in FIG. 10B. Here, FIG. 15 is a schematic diagram showing a section cut along the E-E' line of FIG. 11.

There is not any special restriction on the width of each of the wires 31b, 32b, 41b and 42b, and, for example, the width is preferably about 0.2 to 1 mm. Moreover, there is not any special restriction on the thickness of each of the wires 31b, 32b, 41b and 42b, and, for example, the thickness is preferably about 5 to 30 μm. Furthermore, examples of the material of each of the wires 31b, 32b, 41b and 42b include platinum, molybdenum and tungsten.

As shown in FIGS. 11 and 16, the particulate matter detection device 400 preferably further includes the heater 33 which is disposed (embedded) in the detection device main body 21 so as to extend along the wall surface of the through hole 22 (the wall surface parallel to the side surface of the detection device main body 21). The heater 33 can heat and oxidize the particulate matter adsorbed by the electrodes. Moreover, during the measurement of the mass of the particulate matter or the like, the inner space of the through hole 22 is adjusted to a desired temperature, and the temperature can be adjusted to stably measure the change of the electric characteristics of the wall forming the through hole. The heater 33 may have a broad film-like shape, but as shown in FIG. 16, a linear metal material is preferably disposed in a wavelike shape, and the tip portion of the material may be U-turned. The heater having such a shape can uniformly heat the inside of the through hole. Examples of the material of the heater 33 include platinum, molybdenum and tungsten. The heater 33 is preferably embedded in the detection device main body 21 so as to extend along the wall surface of the through hole 22, but as shown in FIGS. 14, 16, the position of the heater is not limited to the position provided with the through hole 22, and the heater may be formed so as to extend on the side of the other end 21b of the detection device main body 21. This produces advantages that a temperature difference between the inside of the through hole and the vicinity of the through hole can be decreased and that an element does not easily break down even during immediate heating. The heater 33 can preferably raise the temperature of the inner space of the through hole 22 up to 650° C.

In the particulate matter detection device 400, at least one heater 33 is preferably disposed at a position on a side opposite to a side provided with the through hole 22 in at least one of the first electrode 31 and the second electrode 32. In the particulate matter detection device 400 shown in FIG. 11, the heater 33 is disposed at a position on the side of the second electrode 32 opposite to the side provided with the through hole 22. Thus, the heater 33 is disposed at the position on the side of at least one of the first electrode 31 and the second electrode 32 opposite to the side provided with the through hole 22, whereby the electric discharge can be caused between the first electrode 31 and the second electrode 32 without being electrically influenced by a conductor constituting the heater 33. In FIG. 11, one heater 33 is disposed, but a plurality of heaters may be provided on the side of the second electrode 32 opposite to the side provided with the through hole 22. Moreover, in FIG. 11, the heater 33 is provided on the side of the second electrode 32 opposite to the side provided with the through hole 22, but at least one heater 33 is preferably provided at a position on the side of each (both) of the first electrode 31 and the second electrode 32 opposite to the side provided with the through hole 22. The arrangement and number of the heaters 33 may be set to the arrangement and number necessary for achieving an object to adjust the temperature or to oxidize and remove the collected particulate matter.

As shown in FIG. 16, the heater 33 is connected to wires 33b, 33b, and the wires 33b, 33b are interlayer-connected to the takeoff terminals 33a, 33a shown in FIG. 10B, respectively. The takeoff terminal 33a of the heater 33 is preferably disposed in the other end 21b of the detection device main body 21 to avoid the influence of heat when the one end 21a of the detection device main body 21 is heated, in the same manner as in the takeoff terminals 31a, 32a of the first electrode 31 and the second electrode 32. In FIG. 10B, the takeoff terminals 41a, 42a are disposed at both edges of the side surface of the detection device main body 21 in the width direction of the main body, two takeoff terminals 33a, 33a are arranged in the center of the side surface of the detection device main body 21 in the width direction thereof, and the takeoff terminal 32a is disposed between the takeoff terminal 41a and the takeoff terminal 33a. This arrangement of the takeoff terminals is one preferable configuration of the arrangement, but the present invention is not limited to such arrangement.

When the heater 33 has a linear shape, there is not any special restriction on the width of the linear shape, and, for example, the width is preferably about 0.05 to 1 mm. Moreover, there is not any special restriction on the thickness of the heater 33 and, for example, the thickness is preferably about 5 to 30 μm. There is not any special restriction on the width of the wire 33b and, for example, the width is preferably about 0.7 to 4 mm. Furthermore, there is not any special restriction on the thickness of the wire 33b and, for example, the thickness is preferably about 5 to 30 μm. There is not any special restriction on the width of the takeoff terminal 33a corresponding to the heater 33 and, for example, the width is preferably about 0.1 to 2 mm. In addition, there is not any special restriction on the thickness of the takeoff terminal 33a and, for example, the thickness is preferably about 5 to 1000 μm. Examples of the material of the wire 33b and the takeoff terminal 33a include nickel, platinum, tungsten, molybdenum, aluminum, gold, silver, copper, stainless steel and Kovar.

Moreover, in the particulate matter detection device 400, the voltage is preferably applied between the first electrode 31 and the pair of measurement electrodes 41, 42 to cause the electric discharge in the through hole 22, whereby the particulate matter adsorbed by the electrodes can be oxidized and removed. The discharge of the electricity caused in the through hole is preferably the discharge of the electricity along the surface of the dielectric material which covers the one surface of the first electrode 31. As conditions for causing the discharge of the electricity in a case where the particulate matter is oxidized and removed, an electric field strength is preferably 10 to 200 kV/cm, and the amount of energy to be introduced is 0.05 to 10 J/μg with respect to a treatment target. To cause such electric discharge, the device preferably further includes a power source for removal.

The particulate matter detection device 400 further includes a power source for heating connected to the takeoff terminal 33a of the heater 33. Examples of the power source for heating include a direct-current power source.

Figure 17:
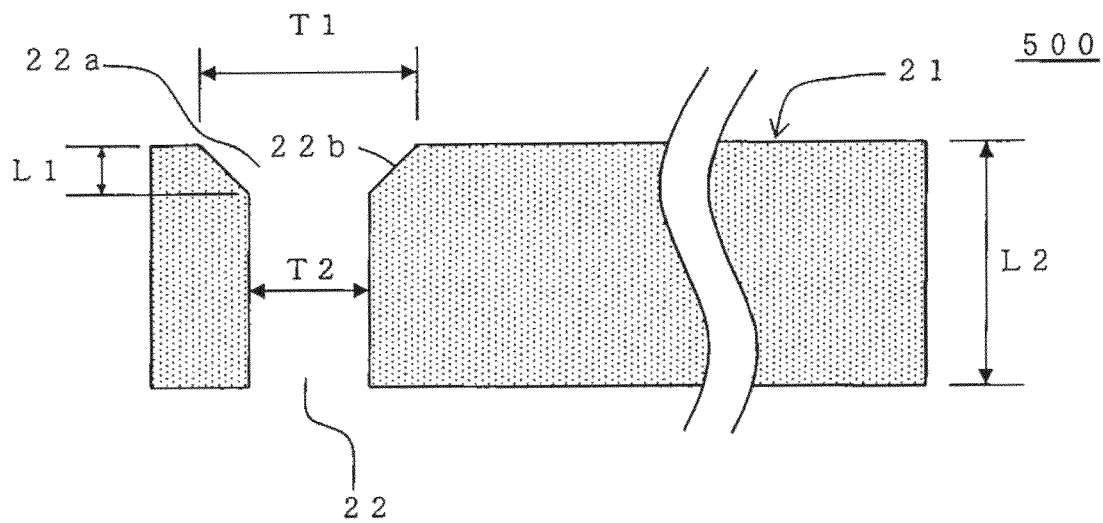
FIG. 17 is a schematic diagram showing a further embodiment of the first particulate matter detection device according to the present invention, and corresponds to the schematic diagram showing the section of the further embodiment of the particulate matter detection device of the present invention shown in FIG. 14.

In the particulate matter detection device 400, there is not any special restriction on the shape and size of the through hole 22 as long as the exhaust gas can pass through the through hole and the amount of the particulate matter can be measured. For example, the length of the through hole 22 in the longitudinal direction of the detection device main body is preferably about 2 to 20 mm, and the width of a portion of the through hole 22 sandwiched between the first electrode 31 and the second electrode 32 (the length in a direction vertical to both of the longitudinal direction of the detection device main body and the gas circulating direction) is preferably about 3 to 30 mm. In such a range, the exhaust gas including the particulate matter can sufficiently be circulated through the through hole 22, and it is possible to cause the electric discharge effectively for electrically charging the particulate matter in the through hole 22. Moreover, as to the shape of the through hole 22, at least one of an inlet portion of the through hole 22 into which the fluid flows and an outlet portion of the through hole out of which the fluid flows is preferably enlarged. At least one of the inlet portion of the through hole 22 into which the fluid flows and the outlet portion of the through hole out of which the fluid flows is enlarged, whereby it is possible to more efficiently allow the exhaust gas circulating through the pipe or the like to flow into (a case where the inlet portion is enlarged) and/or flow out of (a case where the outlet portion is enlarged) the through hole of the particulate matter detection device. In another embodiment (a particulate matter detection device 500) of the first particulate matter detection device according to the present invention shown in FIG. 17, an only inlet portion 22a of a through hole 22 into which the fluid flows is enlarged to form an enlarged portion 22b. Moreover, in the particulate matter detection device 500 shown in FIG. 17, the through hole 22 is enlarged so as to spread in the longitudinal direction of the detection device main body 21, but may be enlarged so as to spread in the thickness direction of the detection device main body 21. FIG. 17 is a schematic diagram showing a further embodiment of the first particulate matter detection device according to the present invention, and corresponds to the schematic diagram showing the section of the further embodiment (the particulate matter detection device 400) of the first particulate matter detection device according to the present invention shown in FIG. 14.

An enlarged width (the width of the outermost tip portion of the through hole 22 in the gas circulating direction) T1 of the enlarged portion 22b is preferably 2 to 200% of a width T2 of a portion of the through hole 22 which is not enlarged. Moreover, a depth (the depth of the enlarged portion) L1 of the enlarged portion 22b in the gas circulating direction of the through hole 22 is preferably 5 to 30% of a length L2 of the through hole 22 in the gas circulating direction.

Figure 18A:
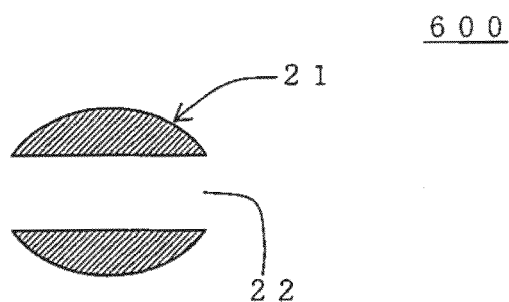
FIG. 18A is a schematic diagram showing the section of the further embodiment of the first particulate matter detection device according to the present invention, the section crossing a central axis at right angles and including a through hole.
Figure 18B:
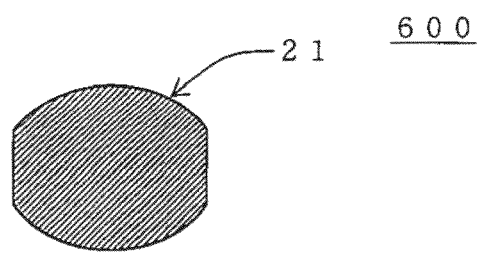
FIG. 18B is a schematic diagram showing the section of the further embodiment of the first particulate matter detection device according to the present invention, and the section crosses the central axis at right angles and does not include any through hole.

As shown in FIGS. 18A and 18B, in a further embodiment (a particulate matter detection device 600) of the first particulate matter detection device according to the present invention, the sectional shape of a detection device main body 21 crossing a central axis thereof at right angles preferably gradually thickens from one end thereof to the center in the extending direction of a through hole 22, becomes thickest in the center, and gradually thins toward the other end. When the detection device main body has such a shape and the gas circulating direction of the through hole is matched with (in parallel with) the circulating direction of an exhaust gas in a pipe, the exhaust gas satisfactorily flows through the pipe. "The center" of the particulate matter detection device (the detection device main body) in the extending direction of the through hole is "a region of ⅓" positioned in the center, when the length of the particulate matter detection device in the extending direction of the through hole is divided into three equal lengths. Therefore, "the sectional shape becomes thickest in the center of the particulate matter detection device in the extending direction of the through hole" means that the thickest portion is positioned in the above "region of ⅓ positioned in the center". Here, FIG. 18A is a schematic diagram showing the section of the further embodiment of the particulate matter detection device according to the present invention, the section crossing the central axis at right angles and including the through hole, and FIG. 18B is a schematic diagram showing the section of the further embodiment of the first particulate matter detection device according to the present invention, and the section crosses the central axis at right angles and does not include any through hole.

In the detection device main body 21 of the particulate matter detection device 400, a plurality of tape-like ceramic materials (ceramic sheets) are preferably laminated. In consequence, the plurality of tape-like ceramic materials can be laminated so that each electrode, wire or the like is sandwiched between the ceramic materials, to prepare the particulate matter detection device 400, whereby the particulate matter detection device 400 can efficiently be manufactured.

The particulate matter detection device 400 can exert the effect thereof especially when the particulate matter passing through the through hole 22 is soot discharged from a diesel engine.

The further embodiment (the particulate matter detection device 400) of the above particulate matter detection device is preferably similar to the above embodiment of the first particulate matter detection device according to the present invention except the above-mentioned contents of each element.

[(2) Second Particulate Matter Detection Device] Next, a constitution, function, operation and the like of a second particulate matter detection device according to the present invention will mainly be described.

Figure 19:
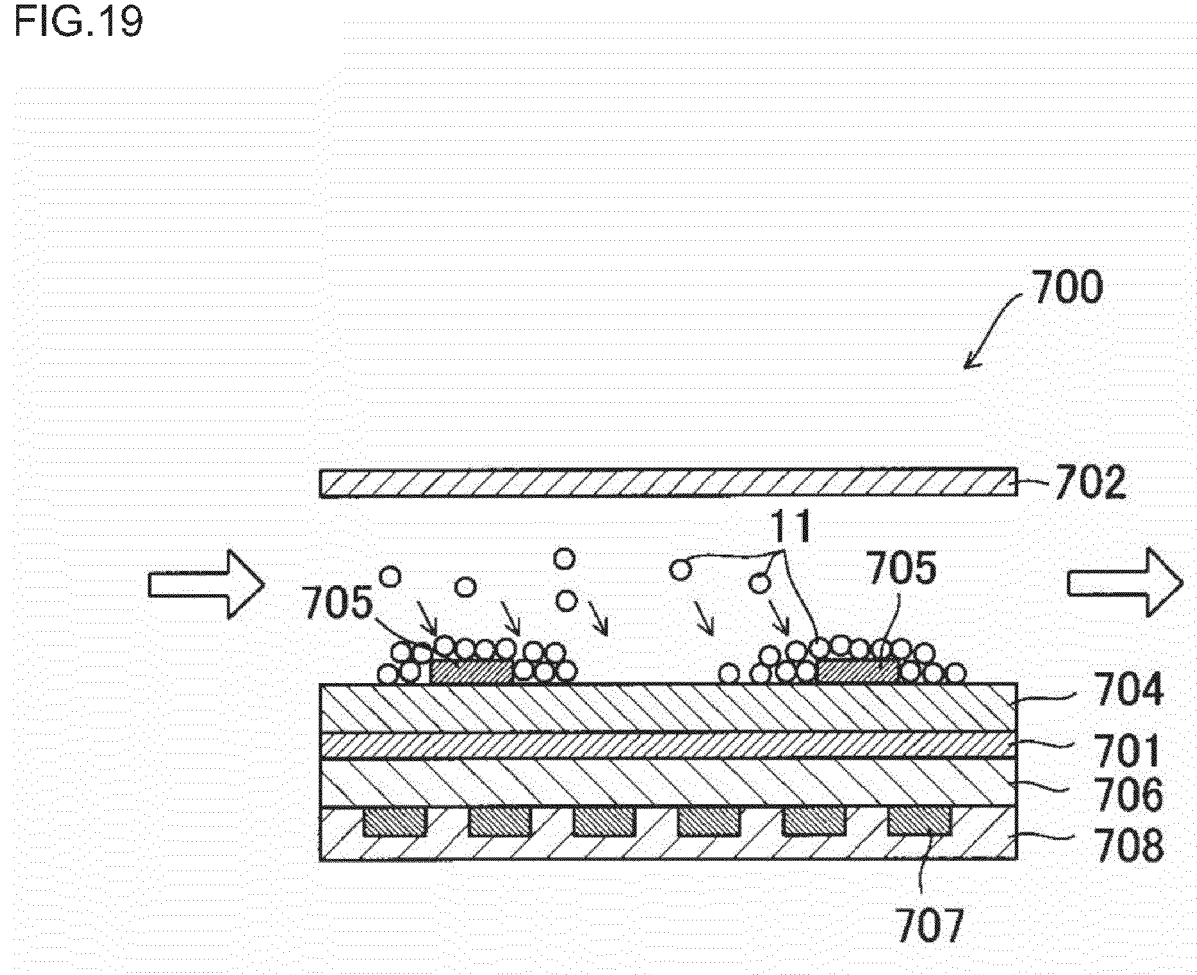
FIG. 19 is a diagram schematically showing one embodiment of a second particulate matter detection device according to the present invention, and is a sectional view showing an only sensor portion.
Figure 25:
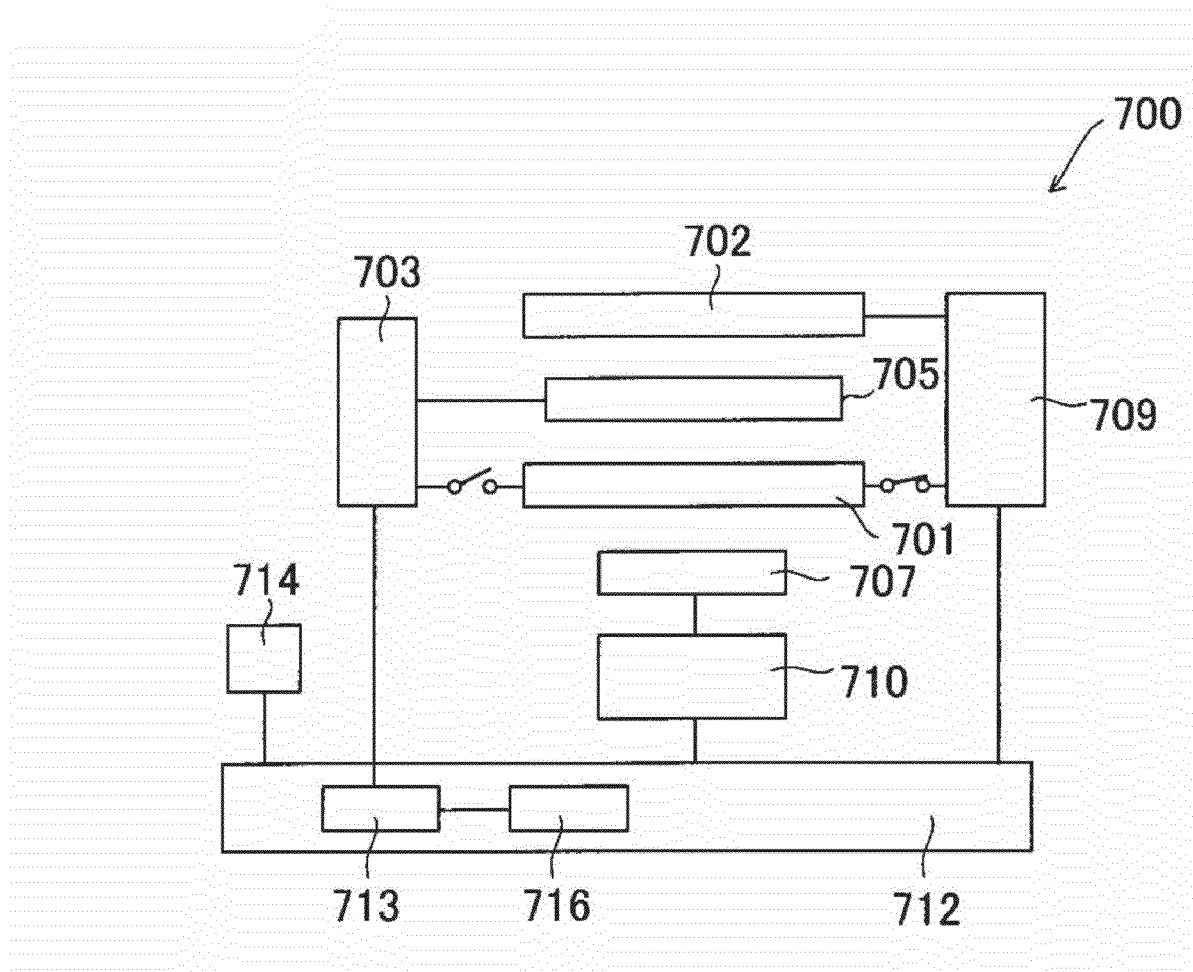
FIG. 25 is a diagram schematically showing the embodiment of the second particulate matter detection device according to the present invention, and is a constitution diagram showing an electric control system.
Figure 26:
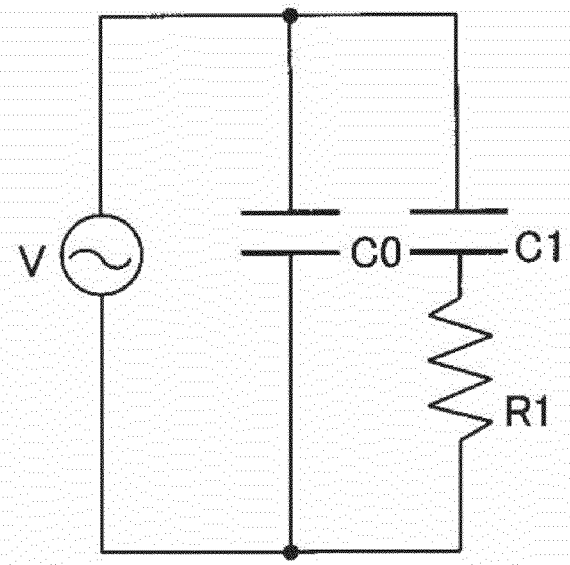
FIG. 26 is a diagram showing an equivalent circuit (an RC circuit) in the particulate matter detection device shown in FIG. 19.

FIGS. 19 and 26 are diagrams schematically showing one embodiment of the second particulate matter detection device according to the present invention. FIG. 19 is a sectional view showing a sensor portion, and FIG. 25 is a constitution diagram showing an electric control system. A particulate matter detection device 700 shown in FIGS. 19 and 25 is constituted of a first electrode 701 having a plate-like shape, a second electrode 702 having a plate-like shape, an inter-electrode dielectric material 704 which covers the upper surface (one surface) of the first electrode 701 (in FIG. 19), a power source 709 which applies a voltage between the first electrode 701 and the second electrode 702, a measurement counter electrode 705 having a plurality of linear potions disposed on the surface of the inter-electrode dielectric material 704, an off-electrode dielectric material 706 which covers the lower surface (the other surface) of the first electrode 701 (in FIG. 19), a heater 707 disposed on the surface (the lower surface in FIG. 19) of the off-electrode dielectric material 706, a power source 710 for the heater which supplies electricity to the heater 707, a sheet-like insulating material 708 which covers, protects and insulates the heater 707 from a portion around the heater, a characteristic measurement unit (means) 703 which measures (the change of) electric characteristics between the first electrode 701 and the measurement counter electrode 705, a particulate matter amount calculation unit (means) 713 which calculates the amount of a particulate matter 11, a particulate matter concentration calculating unit (means) 716 which calculates the concentration of the particulate matter 11, a flow rate meter 714 and a control unit 712. It is to be noted that a portion constituted of the first electrode 701, the second electrode 702, the inter-electrode dielectric material 704, the measurement counter electrode 705, the off-electrode dielectric material 706, the heater 707 and the insulating material 708 shown in FIG. 19 is installed in a through channel through which an exhaust gas including the particulate matter 11 passes. They are referred to a sensor portion sometimes.

In the particulate matter detection device 700, the exhaust gas including the particulate matter 11 flows from the left to the right through a space between the inter-electrode dielectric material 704 which covers the first electrode 701 having the plate-like shape and the second electrode 702 having the plate-like shape as shown (by arrows) in FIG. 19. The flow rate of this exhaust gas is measured by the flow rate meter 714 which is not shown in FIG. 19. In this state, when the power source 709 applies, for example, a direct-current high voltage to the second electrode 702, electric discharge occurs, the exhaust gas (molecules) around the second electrode 702 is separated into positively charged ions and negatively charged ions, and the negatively charged ions move toward the first electrode 701 to which a positive direct-current high voltage has been applied. At this time, the particulate matter 11 included in the exhaust gas collides with the negatively charged ions, and is negatively charged. Then, the charged particulate matter 11 is collected and deposited on the surface of the inter-electrode dielectric material 704 which covers the positive first electrode 701, by an electrostatic force. In this case, the electric characteristics between the first electrode 701 and the measurement counter electrode 705 change in accordance with the degree of the deposition of the particulate matter 11. Therefore, when the change amount of the electric characteristics is acquired, the amount of the particulate matter (PM) collected and deposited on the surface of the inter-electrode dielectric material 704 is obtained. Then, the concentration of the PM in the exhaust gas is obtained from the amount of the deposited PM.

The operation of the particulate matter amount calculation unit 713 can be described with reference to FIG. 8 described above, and the operation of the particulate matter concentration calculating unit 716 can be described with reference to FIG. 9 described above. A change amount E1 of the electric characteristics between the first electrode 701 and the measurement counter electrode 705 has a constant relation between the change amount and an amount W1 of a deposited PM (see FIG. 8). When the characteristic measurement unit 703 acquires the change amount E1 of the electric characteristics, the particulate matter amount calculation unit 713 having a calculating function based on FIG. 8 obtains the amount W1 of the deposited PM. Moreover, when the flow rate of the exhaust gas is set to a constant rate, the amount W1 of the deposited PM has a constant relation between the amount and a PM concentration C1 (see FIG. 9). When the amount W1 of the deposited PM is acquired, the particulate matter concentration calculating unit 716 having a calculating function based on FIG. 9 obtains the PM concentration C1. When the flow rate of the exhaust gas changes, the particulate matter concentration calculating unit 716 corrects the flow rate based on the flow rate obtained by the flow rate meter 714, to obtain the PM concentration C1 from the amount W1 of the deposited PM.

In the particulate matter detection device 700, the particulate matter amount calculation unit 713 and the particulate matter concentration calculating unit 716 are incorporated in the control unit 712. The control unit 712 is mainly constituted of, for example, a sequencer having an electric signal input/output function or the like, and includes, in addition to the particulate matter amount calculation unit 713 and the particulate matter concentration calculating unit 716, a function of inputting the electric signal of the flow rate measured by the flow rate meter 714, to control the power source 710 for the heater or the power source 709 and to control the whole device including the switching of a step and the like.

When, for example, an impedance is obtained as one of the electric characteristics between the first electrode 701 and the measurement counter electrode 705, an alternating-current power source is used, whereby a resistance, a capacitance and an inductance can be measured, respectively. FIG. 26 is a diagram showing an equivalent circuit (an RC circuit) when a voltage V is applied between the first electrode 701 and the measurement counter electrode 705 by use of the alternating-current power source while the particulate matter 11 is present. All the impedance of the circuit is constituted of an only capacitance C0 based on the inter-electrode dielectric material 704 while the particulate matter 11 is not present, but a capacitance C1 and a resistance R1 of the particulate matter 11 are added while the particulate matter 11 is present. Moreover, the capacitance C1 and the resistance R1 change in a constant relation with respect to the amount of the deposited particulate matter 11. Therefore, when the change amount of all the impedance of the circuit is obtained, the amount of the deposited particulate matter 11 is obtained. It is to be noted that inductance components can supposedly mostly be ignored.

In addition, the change of the voltage between the first electrode 701 and the measurement counter electrode 705 may be measured by using a direct-current source, to measure the change of the impedance. The change of the current flowing between the first electrode 701 and the measurement counter electrode 705 or the change of an electric charge accumulated between the first electrode 701 and the measurement counter electrode 705 may be measured by using a direct-current voltage source, to measure the change of the impedance between the first electrode 701 and the measurement counter electrode 705.

The characteristic measurement unit 703 can have an appropriate constitution in accordance with a way of obtaining such electric characteristics and the change of the characteristics. For example, the characteristic measurement unit 703 may be constituted of, for example, an alternating-current power source for applying the voltage to the first electrode 701 and the measurement counter electrode 705, and a measurement unit. Examples of the measurement unit preferably include an LCR meter.

As already described, in the second particulate matter detection device according to the present invention, first the particulate matter 11 in the exhaust gas is collected and deposited on the surface of the inter-electrode dielectric material 704 (a dust collection step), and then the change of the electric characteristics between the first electrode 701 and the measurement counter electrode 705 is measured (a measurement step). The particulate matter is detected or the amount of the particulate matter is obtained mainly through the two steps (in addition, there is a removal step of removing the particulate matter 11 as described later). Moreover, the first electrode 701 functions as an electrode for dust collection in the dust collection step, and functions as an electrode for measurement in the measurement step. Therefore, the connection of the first electrode 701 needs to be switched for each step (see FIG. 25). That is, in the dust collection step, the first electrode 701 is disconnected from the characteristic measurement unit 703, and in the measurement step, the first electrode 701 is disconnected from the power source 709. The control unit 712 manages and controls these steps.

A distance between the inter-electrode dielectric material 704 and the second electrode 702 forming the exhaust gas flowing space is preferably 0.5 to 50 mm, more preferably 0.6 to 40 mm. When the distance is set to such a range, the electricity can more efficiently be discharged, and the particulate matter can more efficiently be collected. When the distance between the inter-electrode dielectric material 704 and the second electrode 702 is shorter than 0.5 mm, a dust collection ratio decreases, and a measurement accuracy deteriorates sometimes. When the distance is longer than 50 mm, a higher voltage is necessary, and energy is wasted sometimes.

The power source 709 supplies a stable direct-current voltage or alternating-current voltage between the first electrode 701 and the second electrode 702 so that the electric discharge can be caused. As the power source 709, for example, a power source using a power source circuit by a flyback system or the like may be employed. In this case, the energy is accumulated from an input-side power source to a transformer, and the accumulated energy can be discharged to an output side to supply a high direct-current voltage. In the power source circuit by the flyback system, the accumulation and discharge of the energy in and from the transformer are controlled by a transistor or the like, and an output-side current is rectified by a diode.

Figure 23:
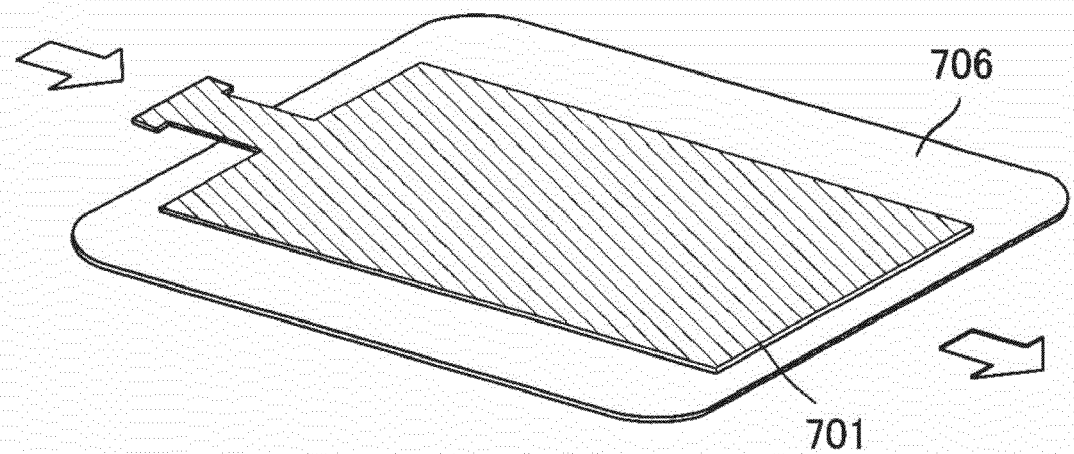
FIG. 23 is a diagram schematically showing the embodiment of the second particulate matter detection device according to the present invention, and is a perspective view showing an off-electrode dielectric material and a first electrode.

FIG. 23 is a perspective view showing the off-electrode dielectric material 706 and the first electrode 701. In FIG. 23, arrows show the flow direction of the exhaust gas. The first electrode 701 performs the formation of an electric field and/or the discharge of electricity as a counter electrode of the second electrode 702, and performs a function of a member for sucking and collecting the electrically charged particulate matter 11. As shown in FIG. 23, the plate-like first electrode 701 in the particulate matter detection device 700 has a substantially rectangular shape, but examples of the shape that can be employed include a polygonal shape such as a pentangular shape, a circular shape, an elliptic shape, a track shape, a shape having unevenness in the outer periphery thereof and a shape including one or a plurality of slits.

The plate-like second electrode 702 is not shown in a perspective view, but has a substantially rectangular shape in the same manner as in the first electrode 701. In the same manner as in the first electrode 701, examples of the shape of the second electrode that can be employed include a polygonal shape such as a pentangular shape, a circular shape, an elliptic shape, a track shape, a shape having unevenness in the outer periphery thereof and a shape including one or a plurality of slits.

The measurement counter electrode 705 having a plurality of linear portions is disposed so as to be long in a direction vertical to the direction in which the exhaust gas flows (arrows in FIG. 19). A distance between the first electrode 701 and the measurement counter electrode 705 is set to a range in which it is possible to clearly measure the change of the electric characteristics between the first electrode 701 and the measurement counter electrode 705 generated when collecting the particulate matter 11 by the first electrode 701. The distance is, for example, about 0.2 to 10 mm.

Figure 24:
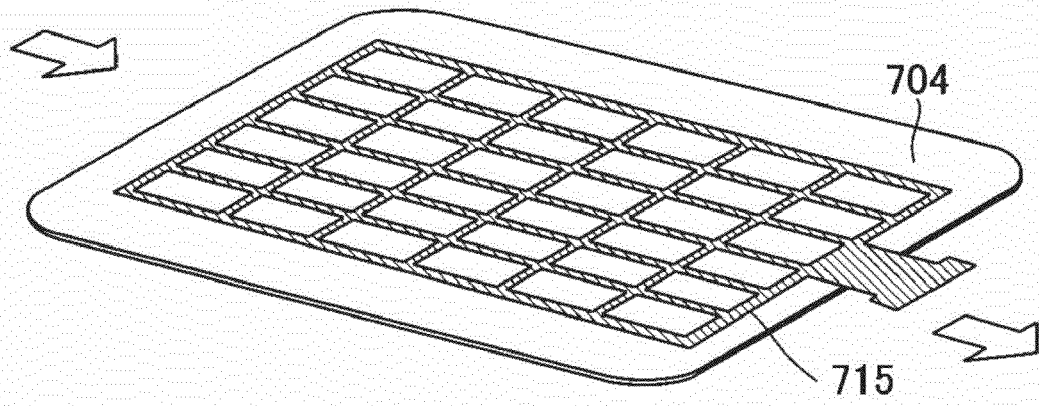
FIG. 24 is a diagram schematically showing the embodiment of the second particulate matter detection device according to the present invention, and is a perspective view showing another configuration of a measurement counter electrode.

FIG. 24 is a perspective view showing another configuration of the measurement counter electrode having a plurality of linear portions. In FIG. 24, arrows show the flow direction of the exhaust gas. A measurement counter electrode 715 shown in FIG. 24 has a lattice-like shape, and facing portions are present in two directions. In addition, the measurement counter electrode 715 is disposed over the whole surface of an inter-electrode dielectric material 704. In the second particulate matter detection device according to the present invention, from a viewpoint that the measurement sensitivity and measurement accuracy of the electric characteristics be improved, it is not preferable that a distance between the linear measurement counter electrodes is long. On the other hand, the measurement counter electrode is preferably disposed at positions corresponding to all of exhaust gas flowing spaces. The measurement counter electrode 715 shown in FIG. 24 embodies such a preferable configuration.

Turning back to the description of the particulate matter detection device 700. The shape and size of the heater 707 may be determined so that all of the particulate matter 11 collected by the surface of the inter-electrode dielectric material 704 can be burnt.

The heater 707 is used not only when the particulate matter 11 is oxidized and removed but also when the change of the electric characteristics between the first electrode 701 and the measurement counter electrode 705 is measured, so that the heater is not influenced by water of dew condensation or the like. For example, when the electrodes are appropriately heated during the detection of the impedance change or the electric discharge, the water can be prevented from being attached to the first electrode 701 and the measurement counter electrode 705. At this time, a heating temperature is preferably 200 to 300° C.

From a viewpoint that efficient temperature control can be performed, examples of the power source 710 for the heater preferably include a power source of a step-down chopper system. The power source is especially preferably a switching power source of the step-down chopper system using a self-arc-suppressing type semiconductor switch. In this case, a switching frequency is preferably an audio frequency of 20 kHz or more. Fuel consumption is directly influenced, and hence the current or power of the power source for the heater is preferably set to a smaller value. The power source 710 for the heater preferably has a temperature control function of calculating the temperature of the heater 707 from the voltage and the current.

The insulating material 708 suppresses the release of the heat generated by the heater 707, whereby the heat of the heater 707 can efficiently be used for efficiently burning the particulate matter 11. The thickness of the insulating material 708 is preferably such a thickness as to suppress the release of the heat, for example, about 100 to 1000 μm.

It is to be noted that in the particulate matter detection device 700, instead of or together with the heater 707 and the power source 710 for the heater, it is possible to employ a power source for removal which applies a voltage between the first electrode 701 and the measurement counter electrode 705 to perform the discharge of the electricity along the surface of the inter-electrode dielectric material 704. In this case, it is necessary to construct an electric control circuit different from that for the dust collection step and the measurement step so that the power source for removal is included and the discharge of the electricity along the surface is performed. That is, it is necessary to provide a switching circuit in which the first electrode 701 is disconnected from the characteristic measurement unit 703, and the first electrode 701 is disconnected from the power source 709, respectively, and the first electrode 701 and the measurement counter electrode 705 can be connected to the power source for removal. As the power source for removal, an alternating-current power source or a pulse power source may be employed.

Figure 20:
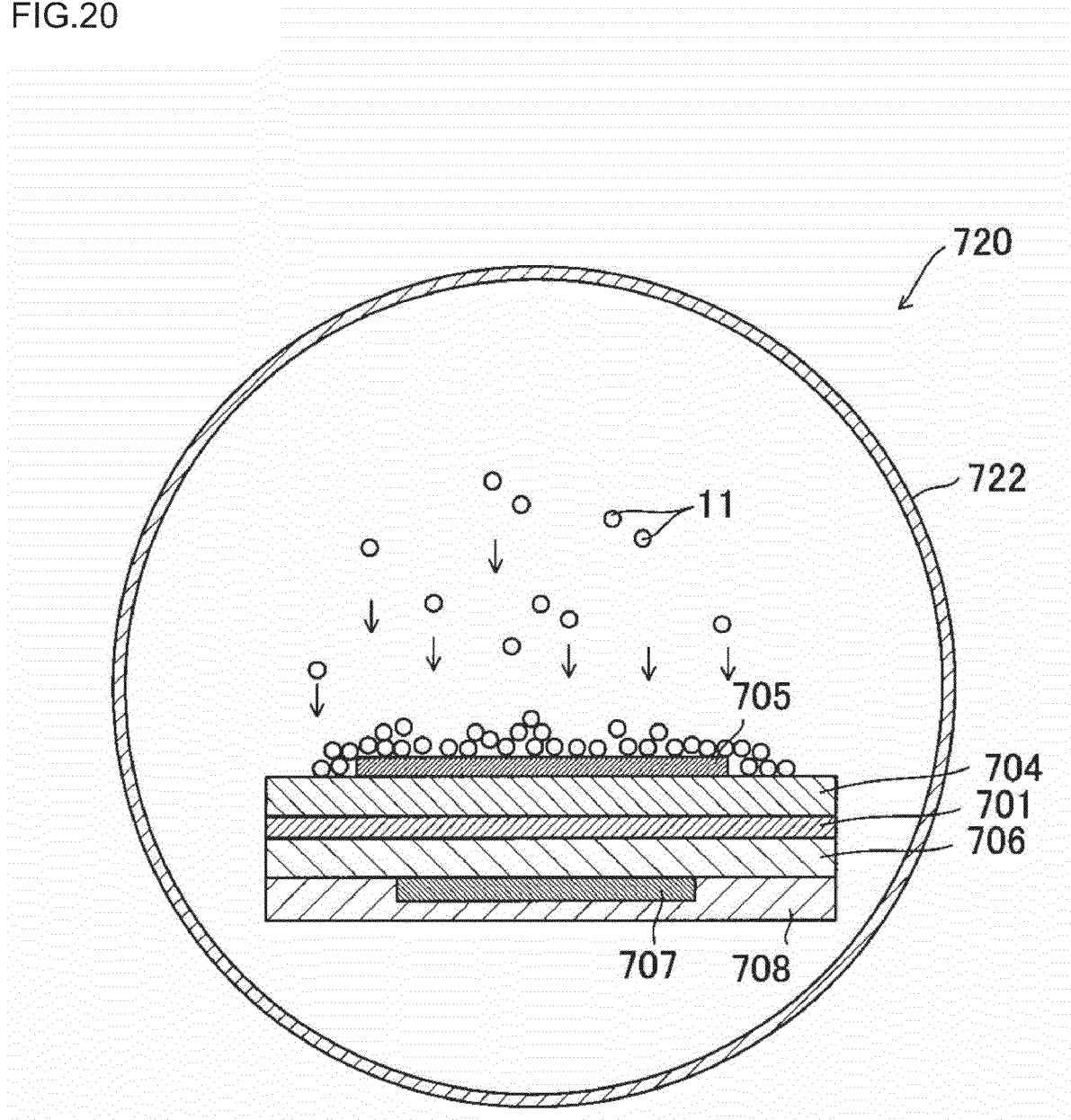
FIG. 20 is a diagram schematically showing another embodiment of the second particulate matter detection device according to the present invention, and is a sectional view showing an only sensor portion.
Figure 21:
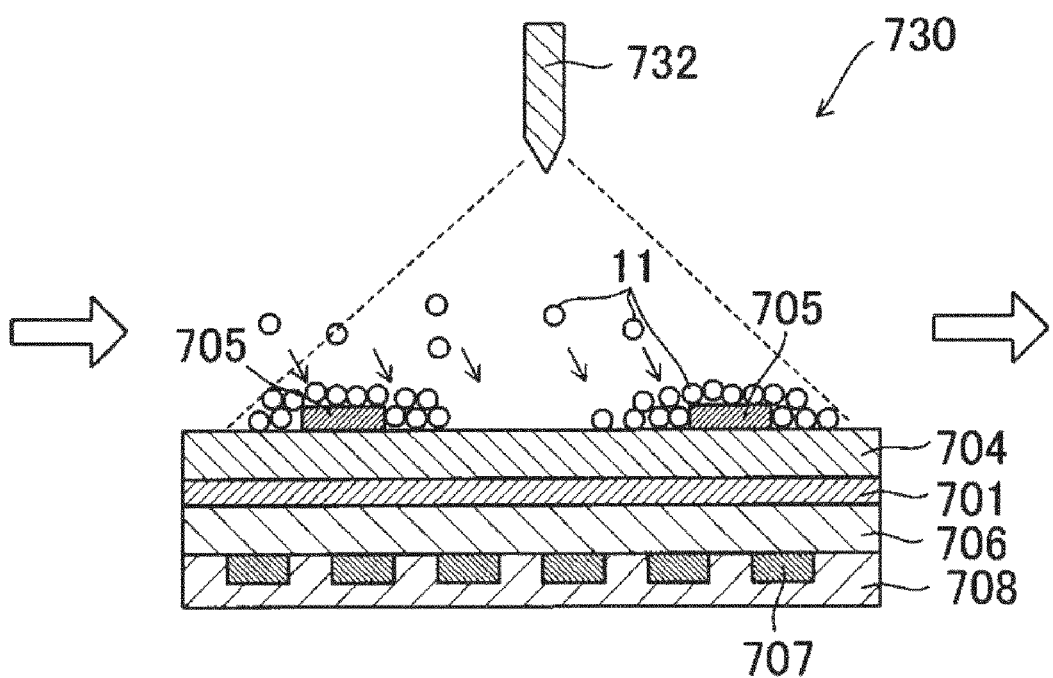
FIG. 21 is a diagram schematically showing still another embodiment of the second particulate matter detection device according to the present invention, and is a sectional view showing an only sensor portion.

The embodiment of the second particulate matter detection device according to the present invention has been described above, but examples of another embodiment include an embodiment in which the second electrode is constituted of a tubular wall surface and an embodiment in which the second electrode having a needle-like or rod-like shape is employed. FIG. 20 is a sectional view showing a particulate matter detection device 720 corresponding to the former embodiment. In FIG. 20, a tubular second electrode 722 constitutes a tubular wall surface. In FIG. 20, a direction in which the exhaust gas flows is a direction from the front to the backside. FIG. 21 is a sectional view showing a particulate matter detection device 730 corresponding to the latter embodiment. A second electrode 732 has a pointed rod-like shape. In the particulate matter detection device 730, corona discharge is performed as electric discharge. In the particulate matter detection devices 720, 730, a device constitution excluding a principle, a function and a second electrode conforms to that of the particulate matter detection device 700, and hence the description thereof is omitted.

Figure 22:
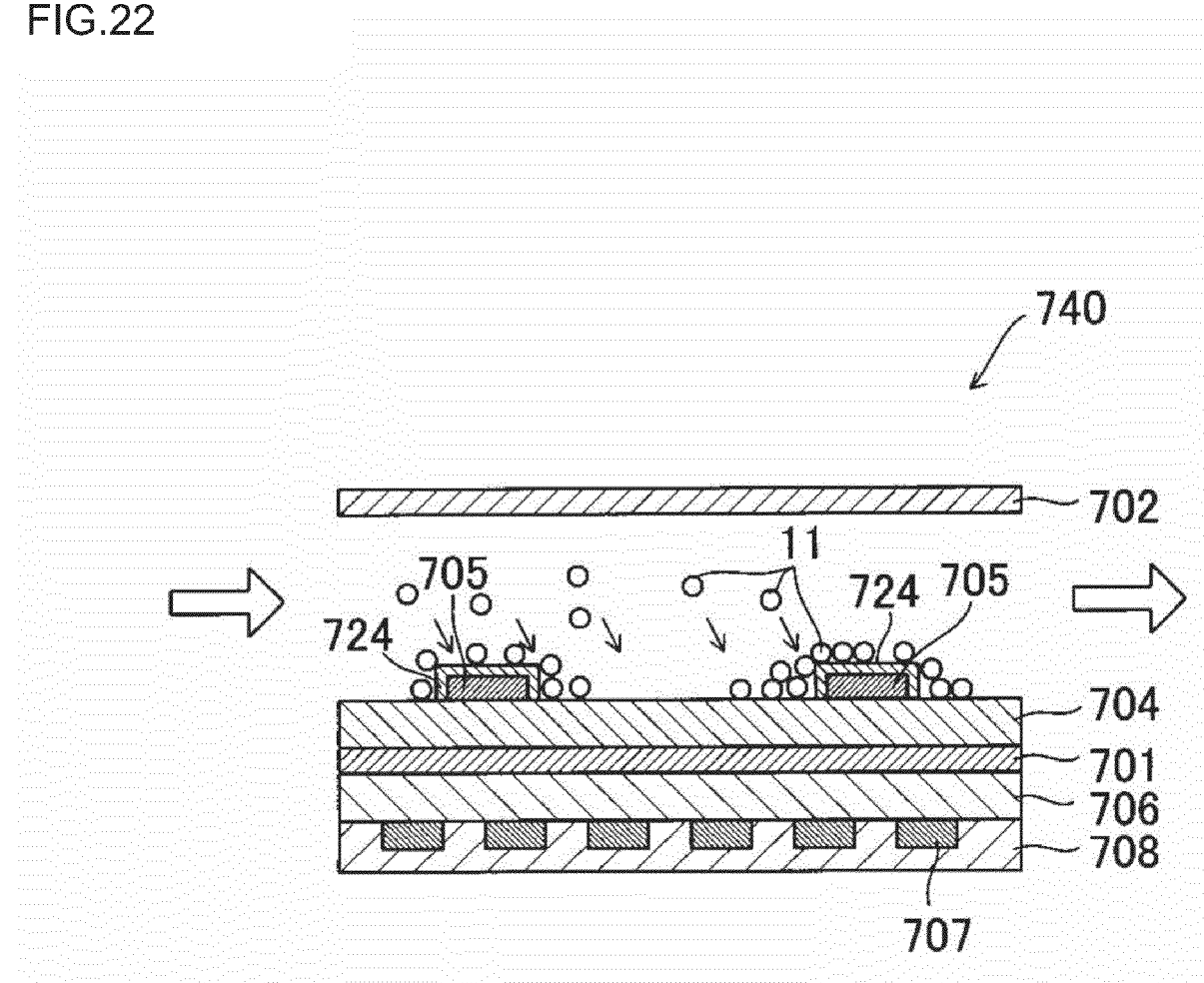
FIG. 22 is a diagram schematically showing a further embodiment of the second particulate matter detection device according to the present invention, and is a sectional view showing an only sensor portion.
Figure 27:
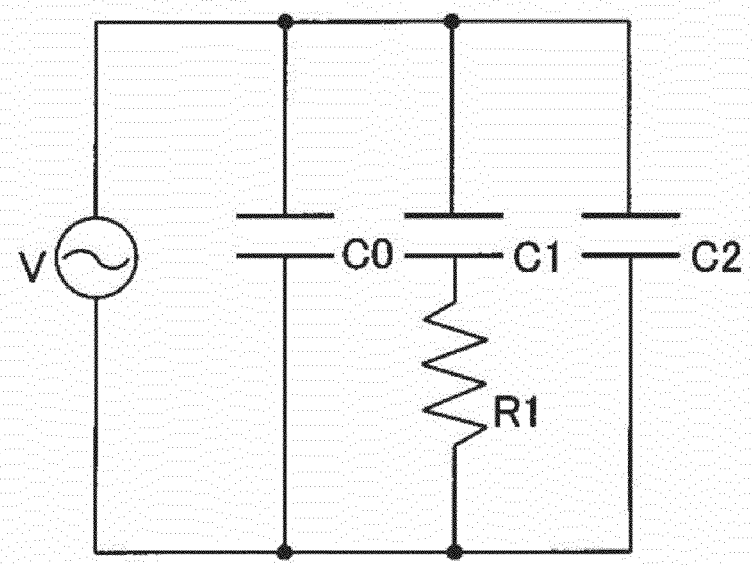
FIG. 27 is a diagram showing an equivalent circuit (an RC circuit) in the particulate matter detection device shown in FIG. 22.

Moreover, examples of a further embodiment of the second particulate matter detection device according to the present invention include a configuration in which the measurement counter electrode is covered with a film-like dielectric material. FIG. 22 is a sectional view showing a particulate matter detection device 740 having such a configuration. FIG. 27 is a diagram corresponding to FIG. 26, and is a diagram showing an equivalent circuit (an RC circuit) when a voltage V is applied between the first electrode 701 and the measurement counter electrode 705 by use of the alternating-current power source while the particulate matter 11 is present. All the impedance of the circuit is constituted of a capacitance C0 based on the inter-electrode dielectric material 704 and a capacitance C2 based on a film-like dielectric material 724 which covers the measurement counter electrode while the particulate matter 11 is not present, but a capacitance C1 and a resistance R1 of the particulate matter 11 are added while the particulate matter 11 is present. Moreover, the capacitance C1 and the resistance R1 change in a constant relation with respect to the amount of the deposited particulate matter 11. Therefore, when the change amount of all the impedance of the circuit is obtained, the amount of the deposited particulate matter 11 is obtained in the same manner as in the particulate matter detection device 700.

[(3) Third Particulate Matter Detection Device] Next, a constitution, function, operation and the like of a third particulate matter detection device according to the present invention will mainly be described.

Figure 28:
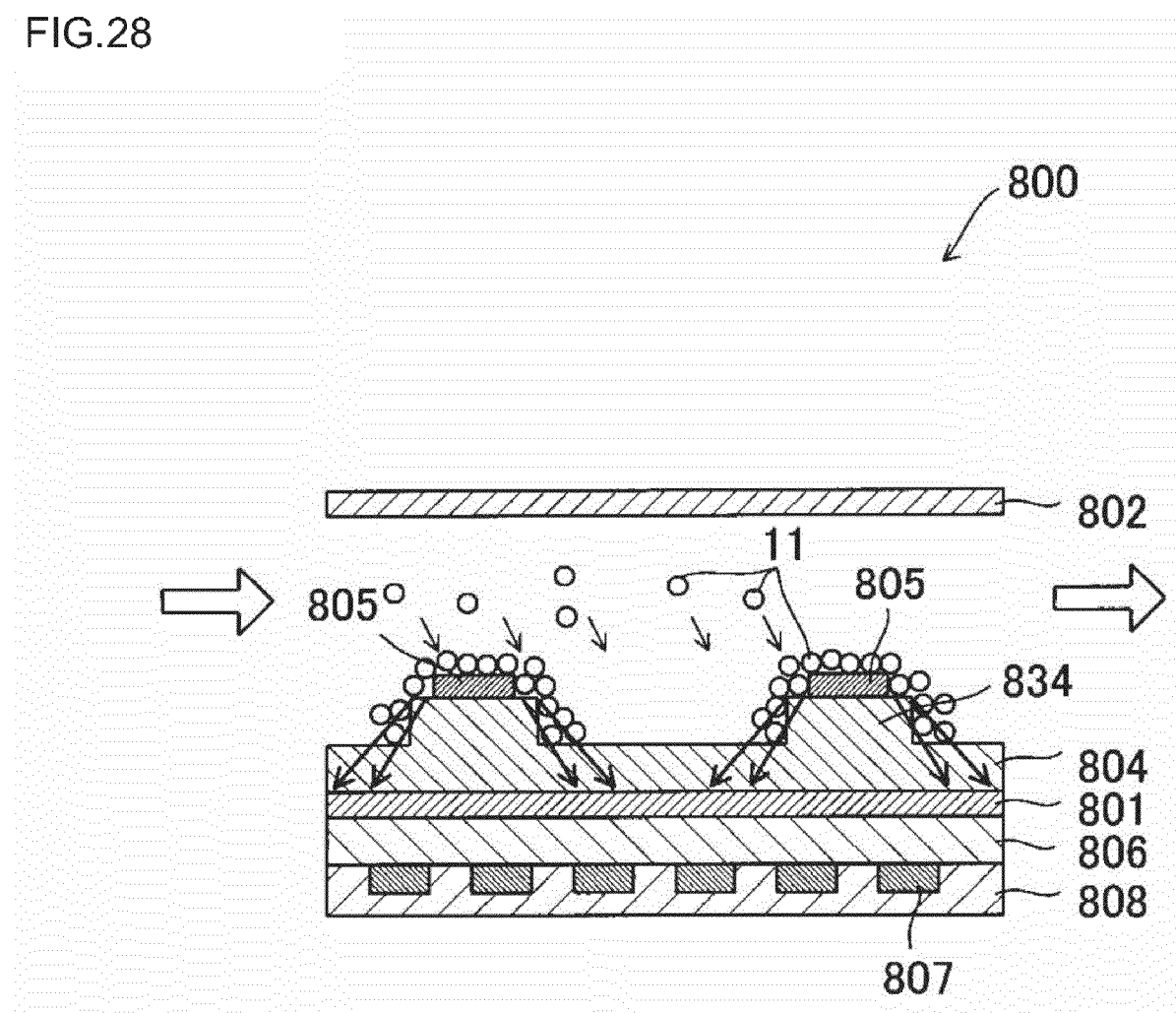
FIG. 28 is a diagram schematically showing one embodiment of a third particulate matter detection device according to the present invention, and is a sectional view showing an only sensor portion.
Figure 33:
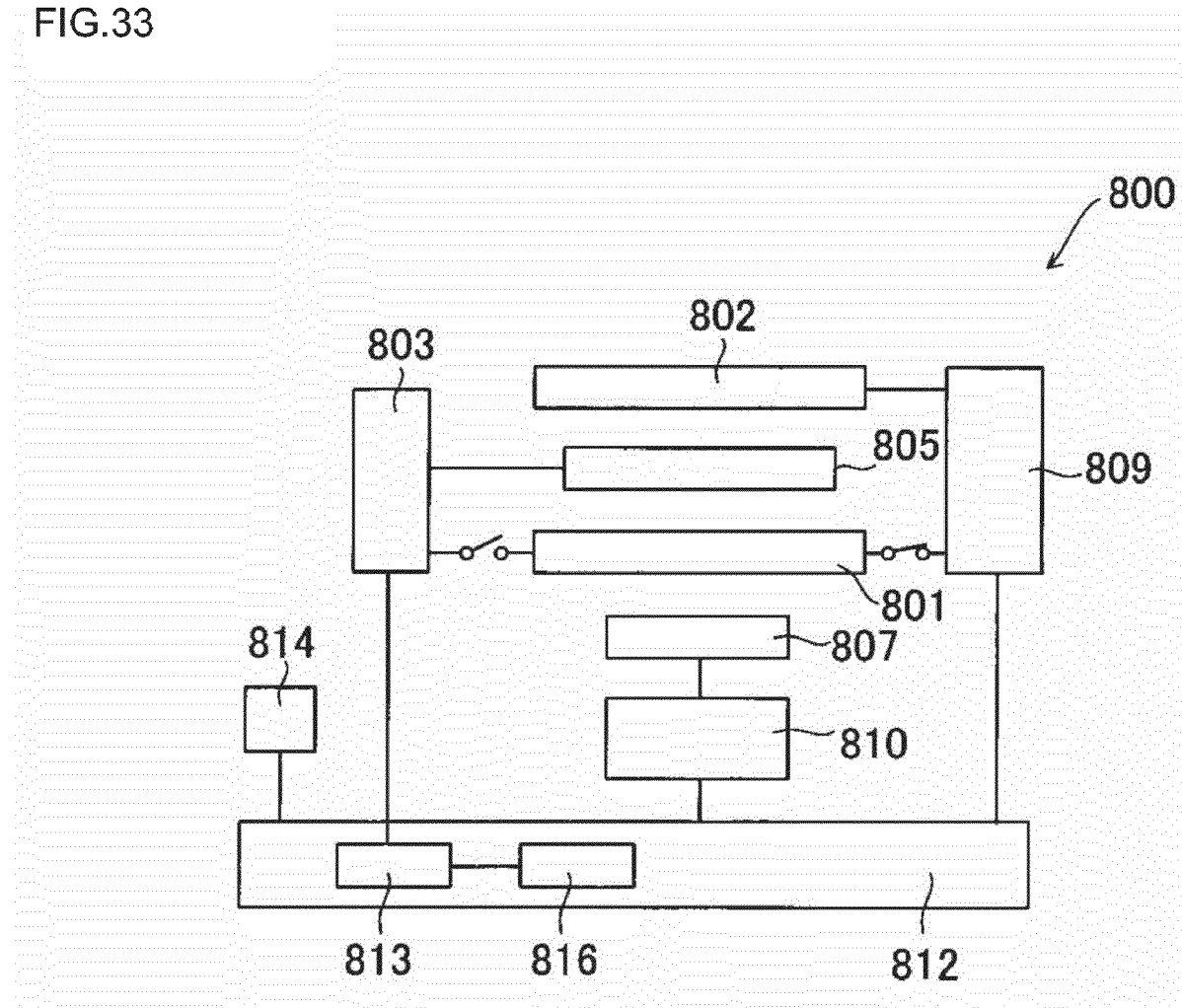
FIG. 33 is a diagram schematically showing the embodiment of the third particulate matter detection device according to the present invention, and is a constitution diagram showing an electric control system.

FIGS. 28 and 33 are diagrams schematically showing one embodiment of the particulate matter detection device according to the present invention. FIG. 28 is a sectional view showing a sensor portion, and FIG. 33 is a constitution diagram showing an electric control system. A particulate matter detection device 800 shown in FIGS. 28 and 33 is constituted of a first electrode 801 having a plate-like shape, a second electrode 802 having a plate-like shape, an inter-electrode dielectric material 804 which covers the upper surface (one surface) of the first electrode 801 (in FIG. 28), a stepped base dielectric material 834 provided on the surface of the inter-electrode dielectric material 804, a power source 809 which applies a voltage between the first electrode 801 and the second electrode 802, a measurement counter electrode 805 raised from the surface of the inter-electrode dielectric material 804 by the stepped base dielectric material 834 and disposed on the surface of the stepped base dielectric material 834, an off-electrode dielectric material 806 which covers the lower surface (the other surface) of the first electrode 801 (in FIG. 28), a heater 807 disposed on the surface (the lower surface in FIG. 28) of the off-electrode dielectric material 806, a power source 810 for the heater which supplies electricity to the heater 807, a sheet-like insulating material 808 which covers, protects and insulates the heater 807 from a portion around the heater, a characteristic measurement unit (means) 803 which measures (the change of) electric characteristics between the first electrode 801 and the measurement counter electrode 805, a particulate matter amount calculation unit (means) 813 which calculates the amount of a particulate matter 11, a particulate matter concentration calculating unit (means) 816 which calculates the concentration of the particulate matter 11, a flow rate meter 814 and a control unit 812. It is to be noted that a portion constituted of the first electrode 801, the second electrode 802, the inter-electrode dielectric material 804, the stepped base dielectric material 834, the measurement counter electrode 805, the off-electrode dielectric material 806, the heater 807 and the insulating material 808 shown in FIG. 28 is installed in a through channel through which an exhaust gas including the particulate matter 11 passes. They are referred to a sensor portion sometimes.

In the particulate matter detection device 800, the exhaust gas including the particulate matter 11 flows from the left to the right through a space between the inter-electrode dielectric material 804 which covers the first electrode 801 having the plate-like shape and the second electrode 802 having the plate-like shape as shown (by arrows) in FIG. 28. The flow rate of this exhaust gas is measured by the flow rate meter 814 which is not shown in FIG. 28. In this state, when the power source 809 applies, for example, a direct-current high voltage to the second electrode 802, electric discharge occurs, the exhaust gas (molecules) around the second electrode 802 is separated into positively charged ions and negatively charged ions, and the negatively charged ions move toward the first electrode 801 to which a positive direct-current high voltage has been applied. At this time, the particulate matter 11 included in the exhaust gas collides with the negatively charged ions, and is negatively charged. Then, the electrically charged particulate matter 11 is collected and deposited on the surface of the inter-electrode dielectric material 804 which covers the positive first electrode 801, by an electrostatic force. In this case, the radially generated electric characteristics (see FIG. 28) between the first electrode 801 and the measurement counter electrode 805 raised from the surface of the inter-electrode dielectric material 804 by the stepped base dielectric material 834 change in accordance with the degree of the deposition of the particulate matter 11. Therefore, when the change amount of the electric characteristics is acquired, the amount of the particulate matter (PM) collected and deposited on the surface of the inter-electrode dielectric material 804 is obtained. Then, the concentration of the PM in the exhaust gas is obtained from the amount of the deposited PM.

The operation of the particulate matter amount calculation unit 813 can be described with reference to FIG. 8 described above, and the operation of the particulate matter concentration calculating unit 816 can be described with reference to FIG. 9 described above. A change amount E1 of the electric characteristics radially occurring between the first electrode 801 and the measurement counter electrode 805 has a constant relation between the change amount and an amount W1 of a deposited PM (see FIG. 8). When the characteristic measurement unit 803 acquires the change amount E1 of the electric characteristics, the particulate matter amount calculation unit 813 having a calculating function based on FIG. 8 obtains the amount W1 of the deposited PM. Moreover, when the flow rate of the exhaust gas is set to a constant rate, the amount W1 of the deposited PM has a constant relation between the amount and a PM concentration C1 (see FIG. 9). When the amount W1 of the deposited PM is acquired, the particulate matter concentration calculating unit 816 having a calculating function based on FIG. 9 obtains the PM concentration C1. When the flow rate of the exhaust gas changes, the particulate matter concentration calculating unit 816 corrects the flow rate based on the flow rate obtained by the flow rate meter 814, to obtain the PM concentration C1 from the amount W1 of the deposited PM.

In the particulate matter detection device 800, the particulate matter amount calculation unit 813 and the particulate matter concentration calculating unit 816 are incorporated in the control unit 812. The control unit 812 is mainly constituted of, for example, a sequencer having an electric signal input/output function or the like, and includes, in addition to the particulate matter amount calculation unit 813 and the particulate matter concentration calculating unit 816, a function of inputting the electric signal of the flow rate measured by the flow rate meter 814, to control the power source 810 for the heater or the power source 809 and to control the whole device including the switching of a step and the like.

When, for example, an impedance is obtained as one of the electric characteristics radially occurring between the first electrode 801 and the measurement counter electrode 805, an alternating-current power source is used, whereby a resistance, a capacitance and an inductance can be measured, respectively. In addition, the change of the voltage radially occurring between the first electrode 801 and the measurement counter electrode 805 may be measured by using a direct-current source, to measure the change of the impedance. The change of the current transmitted through the particulate matter and radially flowing between the first electrode 801 and the measurement counter electrode 805 or the change of an electric charge accumulated between the first electrode 801 and the measurement counter electrode 805 may be measured by using a direct-current voltage source, to measure the change of the impedance between the first electrode 801 and the measurement counter electrode 805.

The characteristic measurement unit 803 can have an appropriate constitution in accordance with a way of obtaining the above electric characteristics and the change of the characteristics. For example, the characteristic measurement unit 803 may be constituted of, for example, an alternating-current power source for applying the voltage to the first electrode 801 and the measurement counter electrode 805, and a measurement unit. Examples of the measurement unit preferably include an LCR meter.

As already described, in the particulate matter detection device according to the present invention, first the particulate matter 11 in the exhaust gas is collected and deposited on the surface of the inter-electrode dielectric material 804 (a dust collection step), and then the change of the electric characteristics between the first electrode 801 and the measurement counter electrode 805 is measured (a measurement step). The particulate matter is detected or the amount of the particulate matter is obtained mainly through the two steps (in addition, there is a removal step of removing the particulate matter 11 as described later). Moreover, the first electrode 801 functions as an electrode for dust collection in the dust collection step, and functions as an electrode for measurement in the measurement step. Therefore, the connection of the first electrode 801 needs to be switched for each step (see FIG. 33). That is, in the dust collection step, the first electrode 801 is disconnected from the characteristic measurement unit 803, and in the measurement step, the first electrode 801 is disconnected from the power source 809. The control unit 812 manages and controls these steps.

A distance between the inter-electrode dielectric material 804 and the second electrode 802 forming the exhaust gas flowing space is preferably 0.5 to 50 mm, more preferably 0.6 to 40 mm. When the distance is set to such a range, the electricity can more efficiently be discharged, and the particulate matter can more efficiently be collected. When the distance between the inter-electrode dielectric material 804 and the second electrode 802 is shorter than 0.5 mm, a dust collection ratio decreases, and a measurement accuracy deteriorates sometimes. When the distance is longer than 50 mm, a higher voltage is necessary, and energy is wasted sometimes.

The power source 809 supplies a stable direct-current voltage or alternating-current voltage between the first electrode 801 and the second electrode 802 so that the electric discharge can be caused. As the power source 809, for example, a power source using a power source circuit by a flyback system or the like may be employed. In this case, the energy is accumulated from an input-side power source to a transformer, and the accumulated energy can be discharged to an output side to supply a high direct-current voltage. In the power source circuit by the flyback system, the accumulation and discharge of the energy in and from the transformer are controlled by a transistor or the like, and an output-side current is rectified by a diode.

Figure 31:
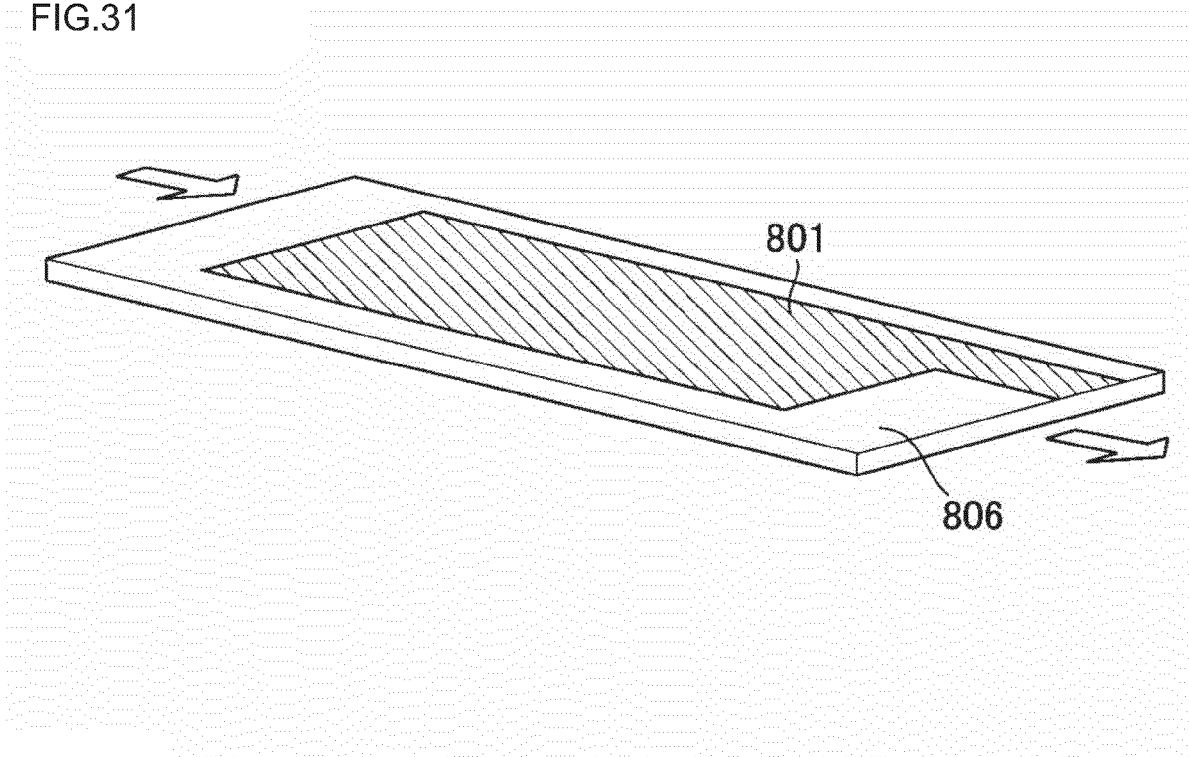
FIG. 31 is a diagram schematically showing the embodiment of the third particulate matter detection device according to the present invention, and is a perspective view showing an off-electrode dielectric material and a first electrode.

FIG. 31 is a perspective view showing the off-electrode dielectric material 806 and the first electrode 801. In FIG. 31, arrows show the flow direction of the exhaust gas. The first electrode 801 performs the formation of an electric field and/or the discharge of electricity as a counter electrode of the second electrode 802, and performs a function of a member for sucking and collecting the electrically charged particulate matter 11. As shown in FIG. 31, the plate-like first electrode 801 in the particulate matter detection device 800 has a substantially rectangular shape, but examples of the shape that can be employed include a polygonal shape such as a pentangular shape, a circular shape, an elliptic shape, a track shape, a shape having unevenness in the outer periphery thereof and a shape including one or a plurality of slits.

The plate-like second electrode 802 is not shown in a perspective view, but has a substantially rectangular shape in the same manner as in the first electrode 801. In the same manner as in the first electrode 801, examples of the shape of the second electrode that can be employed include a polygonal shape such as a pentangular shape, a circular shape, an elliptic shape, a track shape, a shape having unevenness in the outer periphery thereof and a shape including one or a plurality of slits.

The measurement counter electrode 805 has a linear shape, and is disposed so as to be long in a direction vertical to the direction in which the exhaust gas flows (arrows in FIG. 28). A distance between the linear measurement counter electrodes 805 is set to a range in which it is possible to clearly measure the change of the electric characteristics radially occurring between the first electrode 801 and the measurement counter electrode 805 generated when collecting the particulate matter 11 by the first electrode 801. The distance is, for example, about 0.2 to 10 mm.

Figure 32:
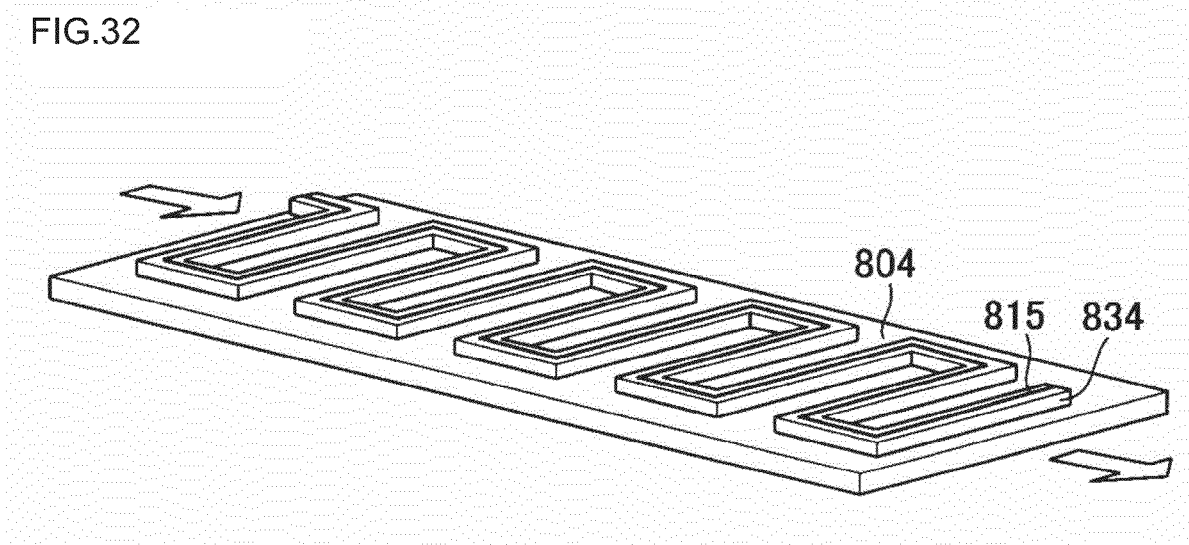
FIG. 32 is a diagram schematically showing the embodiment of the third particulate matter detection device according to the present invention, and is a perspective view showing another configuration of a measurement counter electrode.

FIG. 32 is a perspective view showing another configuration of the measurement counter electrode having a linear shape. In FIG. 32, arrows show the flow direction of the exhaust gas. A measurement counter electrode 815 shown in FIG. 32 is disposed over the whole surface of an inter-electrode dielectric material 804 while bending. The measurement counter electrode 815 is disposed so as to have a stepped portion with respect to the inter-electrode dielectric material 804 on a stepped base dielectric material 834 provided on the surface of the inter-electrode dielectric material 804, and hence the stepped base dielectric material 834 is also provided over the whole surface of the inter-electrode dielectric material 804 while bending. In the particulate matter detection device according to the present invention, from a viewpoint that the measurement sensitivity and measurement accuracy of the electric characteristics be improved, it is not preferable that a distance between the linear measurement counter electrodes is long. On the other hand, the measurement counter electrode is preferably disposed at positions corresponding to all of exhaust gas flowing spaces. The measurement counter electrode 815 shown in FIG. 32 embodies such a preferable configuration.

Turning back to the description of the particulate matter detection device 800. The shape and size of the heater 807 may be determined so that all of the particulate matter 11 collected by the surface of the inter-electrode dielectric material 804 can be burnt.

The heater 807 is used not only when the particulate matter 11 is oxidized and removed but also when the change of the electric characteristics radially occurring between the first electrode 801 and the measurement counter electrode 805 is measured, so that the heater is not influenced by water of dew condensation or the like. For example, when the electrodes are appropriately heated during the detection of the impedance change or the electric discharge, the water can be prevented from being attached to the first electrode 801 and the measurement counter electrode 805. At this time, a heating temperature is preferably 200 to 300° C.

From a viewpoint that efficient temperature control can be performed, examples of the power source 810 for the heater preferably include a power source of a step-down chopper system. The power source is especially preferably a switching power source of the step-down chopper system using a self-arc-suppressing type semiconductor switch. In this case, a switching frequency is preferably an audio frequency of 20 kHz or more. Fuel consumption is directly influenced, and hence the current or power of the power source for the heater is preferably set to a smaller value. Moreover, the power source 810 for the heater preferably has a temperature control function of calculating the temperature of the heater 807 from the voltage and the current.

The insulating material 808 suppresses the release of the heat generated by the heater 807, whereby the heat of the heater 807 can efficiently be used for efficiently burning the particulate matter 11. The thickness of the insulating material 808 is preferably such a thickness as to suppress the release of the heat, for example, about 100 to 1000 μm.

It is to be noted that in the particulate matter detection device 800, instead of or together with the heater 807 and the power source 810 for the heater, it is possible to employ a power source for removal which applies a voltage between the first electrode 801 and the measurement counter electrode 805 to perform the discharge of the electricity along the surface of the inter-electrode dielectric material 804. In this case, it is necessary to construct an electric control circuit different from that for the dust collection step and the measurement step so that the power source for removal is included and the discharge of the electricity along the surface is performed. That is, it is necessary to provide a switching circuit in which the first electrode 801 is disconnected from the characteristic measurement unit 803, and the first electrode 801 is disconnected from the power source 809, respectively, and the first electrode 801 and the measurement counter electrode 805 can be connected to the power source for removal. As the power source for removal, an alternating-current power source or a pulse power source may be employed.

Figure 29:
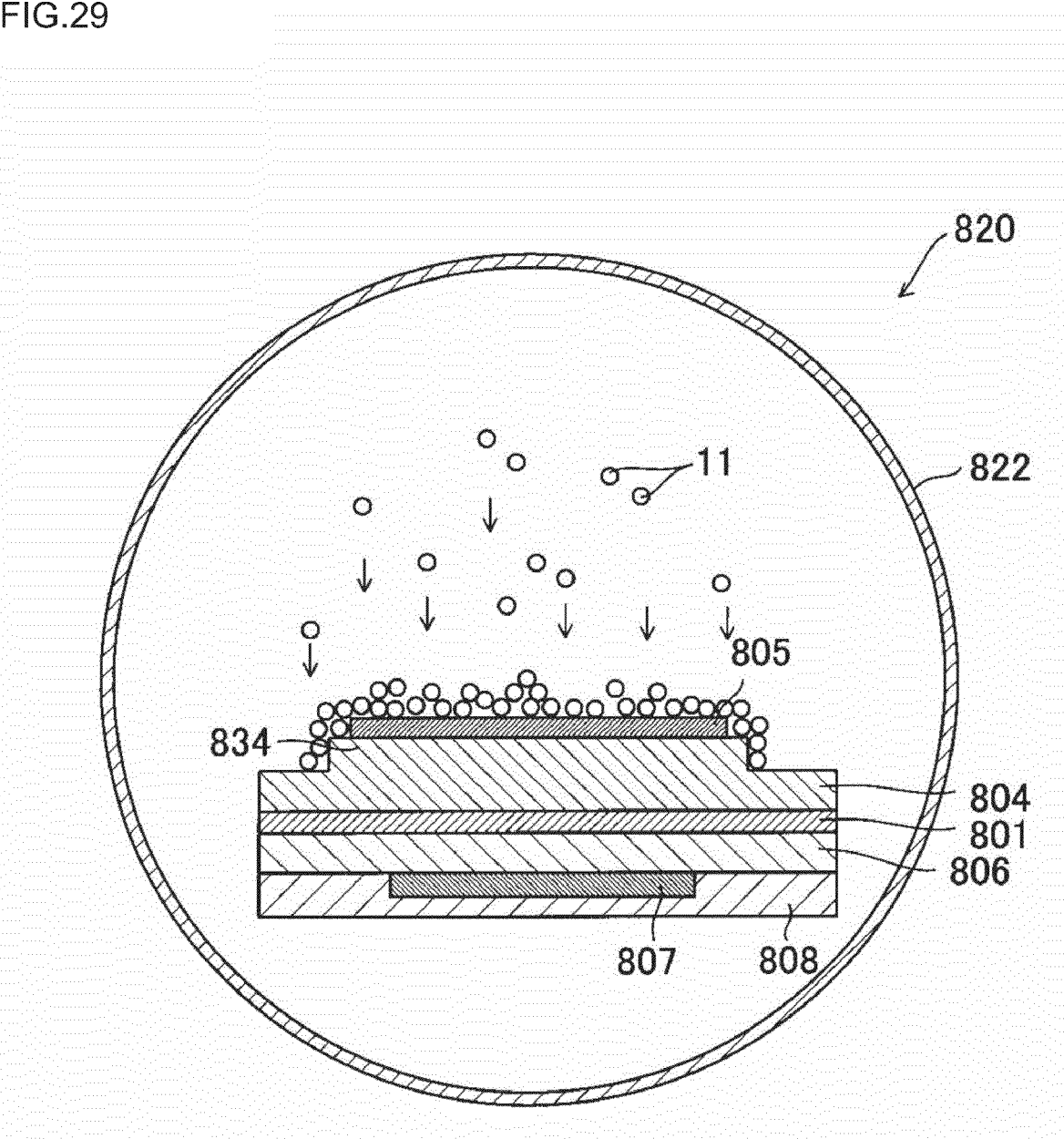
FIG. 29 is a diagram schematically showing another embodiment of the third particulate matter detection device according to the present invention, and is a sectional view showing an only sensor portion.
Figure 30:
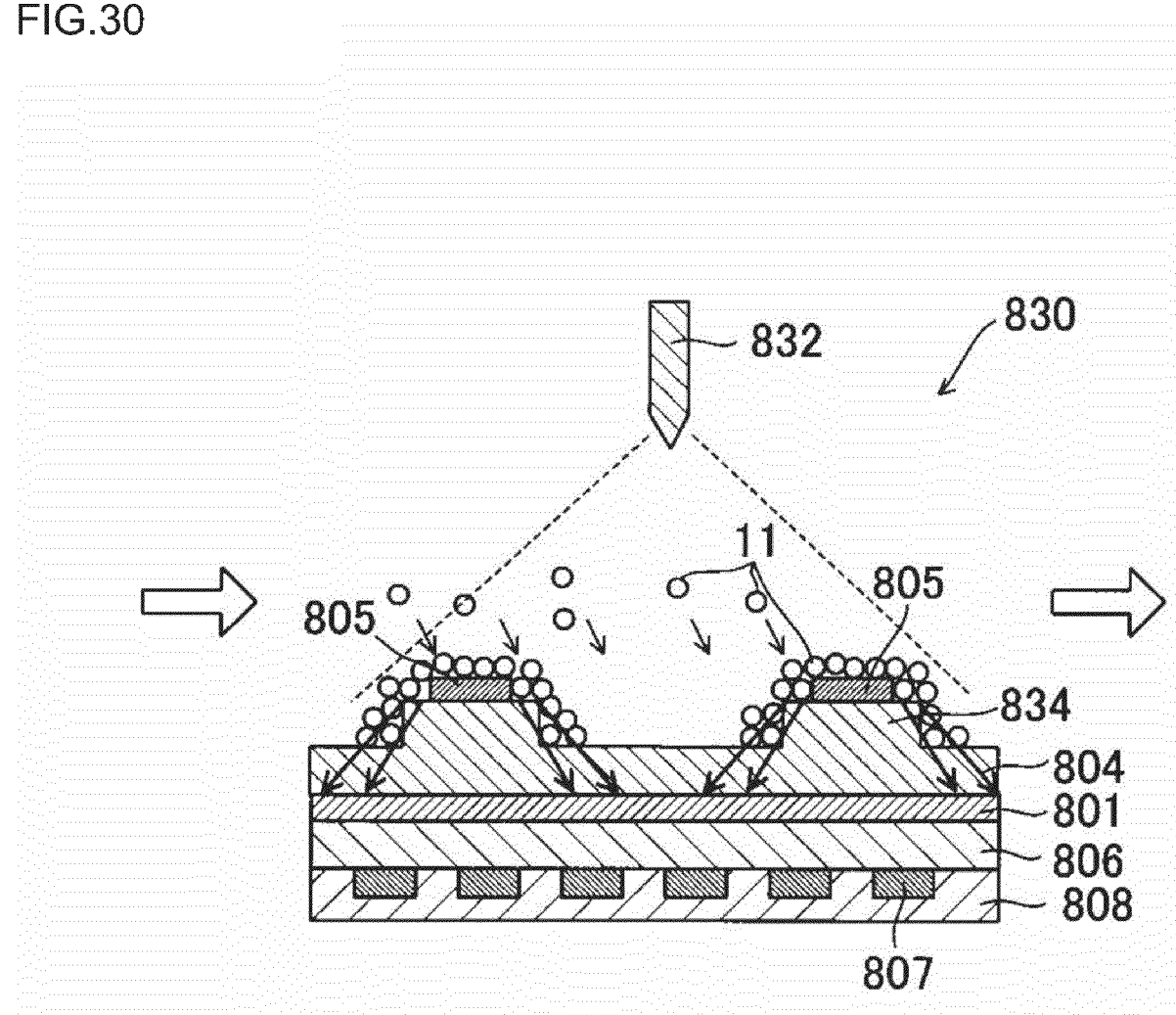
FIG. 30 is a diagram schematically showing still another embodiment of the third particulate matter detection device according to the present invention, and is a sectional view showing an only sensor portion.

The embodiment of the particulate matter detection device according to the present invention has been described above, but examples of another embodiment include an embodiment in which the second electrode is constituted of a tubular wall surface and an embodiment in which the second electrode having a needle-like or rod-like shape is employed. FIG. 29 is a sectional view showing a particulate matter detection device 820 corresponding to the former embodiment. In FIG. 29, a tubular second electrode 822 constitutes a tubular wall surface. In FIG. 29, a direction in which the exhaust gas flows is a direction from the front to the backside. FIG. 30 is a sectional view showing a particulate matter detection device 830 corresponding to the latter embodiment. A second electrode 832 has a pointed rod-like shape. In the particulate matter detection device 830, corona discharge is performed as electric discharge. In the particulate matter detection devices 820, 830, a device constitution excluding a principle, a function and a second electrode conforms to that of the particulate matter detection device 800, and hence the description thereof is omitted. Moreover, examples of a further embodiment of the particulate matter detection device according to the present invention include a configuration in which the measurement counter electrode is covered with a film-like dielectric material.

[(4) Material of Particulate Matter Detection Device] Next, a material forming each constituent element of a particulate matter detection device according to the present invention will be described in accordance with an example of the particulate matter detection device 100. Even in the particulate matter detection device of another embodiment according to the present invention, a similar material may be used.

Examples of the material forming the first electrode 1, the second electrode 2, the measurement electrodes 5, 15 and wires for use in the connection of them preferably include a material containing at least one selected from the group consisting of gold, silver, copper, platinum, palladium, nickel, titanium, manganese, molybdenum and tungsten. The content of these components is preferably 20 vol % or more, more preferably 60 vol % or more. Moreover, as the material forming the first electrode 1, the second electrode 2, the measurement electrodes 5, 15 and the wires for use in the connection of them, stainless steel may be employed.

Examples of the material forming the inter-electrode dielectric material 4, the off-electrode dielectric material 6 and the insulating material 8 preferably include a ceramic material including at least one selected from the group consisting of alumina, magnesium oxide, silicon oxide, silicon nitride, aluminum nitride, zirconia, cordierite, mullite, spinel, aluminum-titanium based oxide, magnesium-calcium-titanium based oxide, barium-titanium-zinc based oxide and barium-titanium based oxide. It is possible to use a ceramic-glass composite material which is obtained by mixing the ceramic material with glass components and which can be fired at a low temperature. The inter-electrode dielectric material 4 and the off-electrode dielectric material 6 made of such a ceramic material do not easily break down, even when temperature fluctuations are generated, and the materials have an excellent resistance to thermal shock. Examples of the insulating material 8 include a ceramic material including at least one selected from the group consisting of alumina, magnesium oxide, silicon oxide, silicon nitride, aluminum nitride, zirconia, cordierite, mullite, spinel, aluminum-titanium based oxide, magnesium-calcium-titanium based oxide, barium-titanium-zinc based oxide and barium-titanium based oxide. It is possible to use a ceramic-glass composite material which is obtained by mixing the ceramic material with glass components and which can be fired at a low temperature. Moreover, these materials may be used in a porous manner or a fiber-like manner.

The measurement electrodes 5, 15 can be covered with the film-like dielectric material, and in this case, examples of a material forming the dielectric material include a ceramic material including at least one selected from the group consisting of alumina, magnesium oxide, silicon oxide, silicon nitride, aluminum nitride, zirconia, cordierite, mullite, spinel, aluminum-titanium based oxide, magnesium-calcium-titanium based oxide, barium-titanium-zinc based oxide and barium-titanium based oxide. It is possible to use a ceramic-glass composite material which is obtained by mixing the ceramic material with glass components and which can be fired at a low temperature.

A material forming the heater 7 is preferably platinum, copper, nickel, titanium, manganese, tungsten, molybdenum, tungsten carbide or the like. In particular, platinum has a high accuracy in a relation between a resistance value and a temperature. Therefore, when platinum is used as the material of the heater 7, accurate temperature control can be achieved.

[(5) Manufacturing Method of Particulate Matter Detection Device] Next, a manufacturing method of a particulate matter detection device according to the present invention will be described in accordance with an example in which the particulate matter detection device 100 is prepared. Even the particulate matter detection device of another embodiment according to the present invention can be manufactured in conformity to the following manufacturing method.

First, a ceramic material of the inter-electrode dielectric material 4, the off-electrode dielectric material 6 and the insulating material 8 is preferably mixed with a binder, a plasticizer, a dispersant and a solvent such as water or an organic solvent if necessary, to prepare a slurry-like forming material. During the mixing, a pot made of alumina and an alumina ball or a mono ball (ball mill) may be used. The material of the inter-electrode dielectric material 4, the off-electrode dielectric material 6 and the insulating material 8 may have the same composition or a different composition. A foaming agent is preferably added to the forming material of the insulating material 8.

As to the binder, methyl cellulose, polyvinyl alcohol, polyethylene oxide or the like may preferably be used as an aqueous binder, and polyvinyl butyral, acrylic resin, polyethylene, polypropylene or the like may preferably be used as a non-aqueous binder. Examples of the acrylic resin include (meth)acrylic resin, (meth)acrylic ester copolymer and acrylic ester-methacrylate ester copolymer. From a viewpoint that the generation of a crack be suppressed during later forming, drying and firing of a green sheet, the amount of the binder to be added is preferably 3 to 20 parts by mass, especially preferably 6 to 17 parts by mass with respect to 100 parts by mass of the ceramic material.

The plasticizer is preferably glycerin, polyethylene glycol, dibutyl phthalate, phthalate-di-2-ethyl hexyl, di-isononyl phthalate or the like. The amount of the plasticizer to be added is preferably 30 to 70 parts by mass, especially preferably 45 to 55 parts by mass with respect to 100 parts by mass of the binder. When the amount is larger than 70 parts by mass, the green sheet becomes excessively soft, and is easily deformed in a step of processing the sheet. When the amount is smaller than 30 parts by mass, the green sheet becomes excessively hard. When the sheet is only bent, the sheet is cracked, and thus handing properties deteriorate sometimes.

In a case of the dispersant, an aqueous dispersant is preferably anionic surfactant, wax emulsion, pyridine or the like, and a p non-aqueous dispersant is preferably fatty acid, ester phosphate, synthetic surfactant or the like. The amount of the dispersant to be added is preferably 0.5 to 3 parts by mass, especially preferably 1 to 2 parts by mass with respect to 100 parts by mass of the ceramic material. When the amount is smaller than 0.5 part by mass, the dispersion properties of the ceramic material deteriorate sometimes, and the green sheet is cracked sometimes. When the amount is larger than 3 parts by mass, the dispersion properties of the ceramic material do not change but impurities during the firing increase.

The organic solvent (medium) is preferably xylene, butanol or the like. The organic solvent may be used alone or as a mixture of a plurality of solvents. The amount of the solvent to be added is preferably 50 to 200 parts by mass, especially preferably 75 to 150 parts by mass with respect to 100 parts by mass of the ceramic material.

Then, the slurry-like forming material is stirred under a reduced pressure, defoamed and further prepared so as to have a predetermined viscosity. From a viewpoint that the material is easily formed into a sheet-like shape, the viscosity as a value measured by a B-type viscometer is preferably 2.0 to 6.0 Pa·s, more preferably 3.0 to 5.0 Pa·s, especially preferably 3.5 to 4.5 Pa·s.

Next, the resultant forming material is formed into a sheet-like shape, thereby forming the green sheet which later constitutes the inter-electrode dielectric material 4, the off-electrode dielectric material 6 and the insulating material 8. A forming method is preferably a doctor blade method, a press forming method, a rolling method, a calendar roll method or the like. The green sheet has a thickness of preferably 50 to 800 µm.

Then, the surface of the resultant green sheet is provided with a conductive paste constituting later the first electrode 1, the pair of measurement electrodes 5, 15, the heater 7 and the necessary wires, and another green sheet is laminated thereon to obtain a laminated green material. The conductive paste can be prepared by adding the binder and a solvent such as terpineol to powder made of the material suitable for the first electrode 1, the pair of measurement electrodes 5, 15, the heater 7 and the necessary wires, and sufficiently kneading the material by use of a triroll mill or the like. Means for providing the conductive paste is preferably a screen printing process. Specifically, to provide the conductive paste, the conductive paste constituting the first electrode 1 and the necessary wires is printed on the one surface of the green sheet constituting the off-electrode dielectric material 6, another green sheet constituting the inter-electrode dielectric material 4 is laminated thereon, and the measurement electrodes 5, 15 and the necessary wires are printed in a desired pattern (for the pattern of the measurement electrodes 5, 15, refer to FIGS. 5 and 6) on the surface of the green sheet constituting the inter-electrode dielectric material 4. On the other hand, the conductive paste constituting the heater 7 and the necessary wire is printed on the other surface of the green sheet constituting the off-electrode dielectric material 6, and another green sheet constituting the insulating material 8 is laminated thereon (see FIG. 28). The green sheets are preferably laminated while pressurized.

Next, the resultant laminated green material is dried at 60 to 150° C., degreased at 400 to 800° C. when the material contains the organic binder, and then fired at 1200 to 1600° C. Thus, the laminated and fired material is obtained which constitutes the particulate matter detection device 100 and which includes the first electrode 1, the inter-electrode dielectric material 4, the measurement electrodes 5, 15, the off-electrode dielectric material 6, the heater 7 and the insulating material 8.

The second electrode 2 is obtained by integrating a commercially available thin plate preferably made of the above-mentioned material with the laminated and fired material via a support member. As the second electrode, a laminated material made of the ceramic material and the conductive paste may be used. As this support member, a sintered material preferably made of the above-mentioned material of the inter-electrode dielectric material 4, the off-electrode dielectric material 6 and the insulating material 8 may be used.

Moreover, to form a cavity (the space) through which the exhaust gas including the particulate matter 11 flows, the laminated and fired material and the support member of the second electrode 2 may be integrated to form a laminated structure. In this case, before obtaining the laminated and fired material, a green sheet forming the cavity and a green sheet forming a top plate may further be laminated on the inter-electrode dielectric material 4 (the measurement electrodes 5, 15) of the above laminated green material, and the inner surface (the surface facing the cavity) of the green sheet forming the top plate is provided with the conductive paste constituting later the second electrode 2 and the necessary wire, thereby obtaining the laminated green material constituted of all the materials, followed by drying, necessary degreasing and firing.

To form the power source 9 for dust collection, the characteristic measurement unit 3 and the power source 10 for the heater, a commercially available material which matches the above-mentioned preferable specifications is purchased. As the flow rate meter 14, a commercially available meter may be employed. The power source 9 for dust collection is connected to the first electrode 1 and the second electrode 2, the characteristic measurement unit 3 is connected to the measurement electrodes 5, 15, and the power source 10 for the heater is connected to the heater 7. The particulate matter amount calculation unit 13 and the particulate matter concentration calculating unit 16 can construct software in a computer such as a sequencer. The control unit 12 may be constructed by the software in a computer such as the sequencer and a control circuit (hardware) to realize the above-mentioned or undermentioned operation of the particulate matter detection device 100. As described above, the particulate matter detection device 100 can be prepared.

Moreover, to prepare the further embodiment (the particulate matter detection device 400) of the first particulate matter detection device according to the present invention shown in FIGS. 10A, 10B, when the forming material is processed into a sheet-like shape to prepare a green sheet, the green sheet is formed into a shape which is long in one direction as shown in FIGS. 12 to 16. The green sheet is laminated so as to obtain the shape of the particulate matter detection device shown in FIGS. 10A, 10B and 11. Then, a plurality of green sheets are formed, and the predetermined position of the surface of the predetermined green sheet is provided with the conductive paste later constituting the first electrode 31 or the like. The green sheets are laminated to obtain a laminated green material. At this time, to form the second electrode 32, the green sheet is provided with a conductive paste later constituting the second electrode 32.

[(6) Method of using Particulate Matter Detection Device]

Next, a method of using the particulate matter detection device according to the present invention will be described in accordance with an example in which the particulate matter detection device 100 is used. Even the particulate matter detection device of another embodiment according to the present invention can be used in conformity to the following using method.

(Dust Collection Step) First, the sensor portion of the particulate matter detection device 100 is installed in, for example, the exhaust system (the exhaust gas tube) of the diesel engine, followed by power source supply, control line connection and the like, whereby the sensor portion is brought into a usable state. Then, the power source 9 for dust collection applies, for example, a direct-current high voltage between the second electrode 2 and the first electrode 1 to electrically charge the particulate matter 11, whereby the particulate matter is deposited on the surface of the inter-electrode dielectric material 4. It is to be noted that when the particulate matter detection device 400 shown in FIGS. 10A, 10B is used, the one end 21a of the particulate matter detection device 400 is inserted into the exhaust gas tube so that the through hole 22 is positioned in the exhaust gas tube, and the particulate matter detection device is preferably disposed so that the other end 21b of the device is positioned outside the exhaust gas tube. At this time, the takeoff terminal 31a of the first electrode 31 is preferably protruded externally from the exhaust gas tube.

A time for applying the high voltage is preferably 0.5 to 120 seconds, more preferably 2 to 10 seconds. When the time is shorter than 0.5 second, the amount of the collected particulate matter 11 decreases, and hence the measurement accuracy of the particulate matter 11 lowers sometimes. When the time is longer than 120 seconds, the amount of the collected particulate matter 11 increases, and hence the amount of the particulate matter 11 cannot easily and correctly be grasped by detecting the change amount of the impedance.

The voltage to be supplied to the first electrode 1 and the second electrode 2 preferably varies in accordance with the distance between the electrodes, but when the voltage to be applied is increased, an electric field strengthens, and a dust collection force increases. On the other hand, insulation, insulation distance and the like raise problems, the device enlarges, and hence the voltage is actually preferably 10 kV or more.

A current flowing between the first electrode 1 and the second electrode 2 by the electric discharge is preferably 1 mA or less, further preferably 1 to 100 μA. When the current is smaller than 1 μA, a dust collection ratio decreases sometimes.

A power for use is preferably small, because the power directly influences fuel consumption. Moreover, in view of the decrease of generated electromagnetic noise or the size of a circuit which causes the electric discharge, the power for use is preferably 10 W or less, more preferably 1 W or less.

(Measurement Step) After the end of the deposition of the particulate matter 11, the application of the high voltage between the second electrode 2 and the first electrode 1 is stopped, and the characteristic measurement unit 3 is operated, whereby the change amount of the impedance between the measurement electrodes 5 and 15 is measured for a time of preferably about 1 to 60 seconds. The amount and concentration of the particulate matter 11 are obtained by this change amount of the impedance. It is to be noted that as described above, the change amount of the impedance between the measurement electrodes 5 and 15 may be measured while depositing the particulate matter on the surface of the inter-electrode dielectric material 4 (while applying the high voltage). However, they are handled in separate measurement modes.

When the characteristic measurement unit 3 is constituted of the alternating-current power source for applying the voltage to the measurement electrodes 5, 15, and the measurement unit, the value of the voltage to be applied from the alternating-current power source is preferably 1 to 60 V, more preferably 2 to 30 V. When the voltage is smaller than 1 V, a detection signal decreases and is easily influenced by the noise. When the voltage is larger than 60 V, a general-purpose IC cannot be used sometimes. A measurement frequency is preferably 300 kHz or less.

(Removal Step) After finishing the measurement of the change amount of the impedance between the measurement electrodes 5 and 15, the heater 7 is operated by the power source 10 for the heater, and the particulate matter 11 deposited on the surface of the inter-electrode dielectric material 4 is oxidized and removed.

When the power source 10 for the heater is the switching power source of the step-down chopper system, a current flowing through the heater 7 is preferably about 0.8 to 4 A, and the power for use is preferably 48 W or less.

A time for oxidizing and removing the particulate matter 11 by the heater 7 is preferably 1 to 600 seconds, especially preferably 3 to 120 seconds. When the time is shorter than 1 second, the oxidation and removal of the particulate matter 11 become insufficient sometimes. When the time is longer than 600 seconds, energy is wasted sometimes.

A temperature during the oxidation and removal of the particulate matter 11 collected by the surface of the inter-electrode dielectric material 4 by the heater 7 is preferably 500 to 900° C., especially preferably 550 to 700° C. When the temperature is lower than 500° C., the particulate matter is not easily oxidized or removed sometimes. When the temperature is higher than 900° C., element life shortens sometimes.

It is to be noted that instead of or together with the heater 7 and the power source 10 for the heater, the particulate matter detection device further includes the power source for removal which applies the voltage between the first electrode 1 and the pair of measurement electrodes 5, 15 to perform the discharge of the electricity along the surface of the inter-electrode dielectric material 4. The collected particulate matter 11 can be oxidized and removed by the discharge of the electricity along the surface. In this case, the voltage for the discharge of the electricity along the surface is preferably 2 to 15 kV, depending on the thickness of the inter-electrode dielectric material 4. The power for use is preferably 10 to 30 W. A time for the discharge of the electricity along the surface is preferably 1 to 600 seconds, especially preferably 3 to 120 seconds. When the time is shorter than 1 second, the oxidation and removal of the particulate matter 11 become insufficient sometimes. When the time is longer than 600 seconds, the energy is wasted sometimes.

As described above, when the dust collection step, the measurement step and the removal step are repeated, the detection of the particulate matter 11 can stably be continued for a long time. It is to be noted that in a case where the exhaust gas of the diesel engine is the target of the particulate matter detection, when conditions such as the rotation number and torque of the diesel engine and the flow rate and temperature of the exhaust gas satisfy specific states, the electric discharge is preferably performed. These conditions can be judged by the control unit 12 (the sequencer or the like), when the information of the diesel engine is input as a signal into the control unit 12 and the information of a thermometer provided in the exhaust gas tube is input as a signal into the control unit 12.

The particulate matter detection device according to the present invention can preferably be utilized as means for detecting the particulate matter included in the exhaust gas from the diesel engine, a gas duct or the like.

What is claimed is:
1. A particulate matter detection device comprising:
a first electrode which has a plate-like shape and whose one surface is covered with a dielectric material; a second electrode disposed on the side of the one surface of the first electrode via a space through which a gas including a particulate matter flows, to perform the formation of an electric field and/or the discharge of electricity by a voltage applied between the first electrode and the second electrode; and a power source which applies the voltage; and a pair of measurement electrodes disposed on the surface of the dielectric material so as to face each other; characteristic measurement means for measuring electric characteristics between the pair of measurement electrodes; and particulate matter amount calculation means for obtaining the amount of the particulate matter collected by the surface of the dielectric material, based on the change amount of the electric characteristics measured by the characteristic measurement means.

2. The particulate matter detection device according to claim 1, wherein the pair of measurement electrodes have a linear shape and are disposed on the surface of the dielectric material so as to be long in a direction vertical to a direction in which the gas including the particulate matter flows and so as to face each other.

3. The particulate matter detection device according to claim 2, wherein each of the pair of measurement electrodes having the linear shape is branched into a plurality of electrodes, respectively, and has a plurality of facing portions.

4. The particulate matter detection device according to claim 1, further comprising:
a dielectric material which covers the other surface of the first electrode having the plate-like shape; and
a heater disposed on the surface of the dielectric material.

5. The particulate matter detection device according to claim 1, further comprising:
a power source for removal which applies a voltage between the first electrode and the pair of measurement electrodes to oxidize and remove the particulate matter by the discharge of the electricity along the surface,
wherein the voltage is applied to perform the discharge of the electricity along the surface of the dielectric material which covers the one surface of the first electrode.

6. The particulate matter detection device according to claim 1, wherein the measurement electrodes are covered with a film-like dielectric material.

7. The particulate matter detection device according to claim 1, further comprising:
a detection device main body constituted of a dielectric material provided with, in one end thereof, a through hole as the space through which the gas including the particulate matter flows, the dielectric material being long in one direction,
wherein the first electrode and the second electrode are embedded in the detection device main body so as to sandwich the through hole therebetween while the one surface of the first electrode faces the side of the through hole, and
the pair of measurement electrodes are disposed on the inner wall surface of the through hole in which the first electrode is embedded.

8. The particulate matter detection device according to claim 7, wherein at least one heater is embedded in a position of at least one of the first electrode and the second electrode on a side opposite to the side on which the through hole is formed.

9. A particulate matter detection device comprising:
a first electrode which has a plate-like shape and whose one surface is covered with a dielectric material; a second electrode disposed on the side of the one surface of the first electrode via a space through which a gas including a particulate matter flows, to perform the formation of an electric field and/or the discharge of electricity by a voltage applied between the first electrode and the second electrode; and a power source which applies the voltage; and a measurement counter electrode disposed on the surface of the dielectric material; characteristic measurement means for measuring electric characteristics between the measurement counter electrode and the first electrode; and particulate matter amount calculation means for obtaining the amount of the particulate matter collected by the surface of the dielectric material, based on the change amount of the electric characteristics measured by the characteristic measurement means.

10. The particulate matter detection device according to claim 9, wherein the measurement counter electrode has a plurality of linear portions, and the plurality of linear portions are disposed on the surface of the dielectric material so as to be long in parallel with a direction vertical to a direction in which the gas including the particulate matter flows.

11. The particulate matter detection device according to claim 10, wherein the measurement counter electrode having the plurality of linear portions has a lattice-like shape.

12. The particulate matter detection device according to claim 9, further comprising:
a dielectric material which covers the other surface of the first electrode having the plate-like shape; and
a heater disposed on the surface of the dielectric material.

13. The particulate matter detection device according to claim 9, further comprising:
a power source for removal which applies a voltage between the first electrode and the measurement counter electrode to oxidize and remove the particulate matter by the discharge of the electricity along the surface,
wherein the voltage is applied to perform the discharge of the electricity along the surface of the dielectric material which covers the one surface of the first electrode.

14. The particulate matter detection device according to claim 9, wherein the measurement counter electrode is covered with a film-like dielectric material.

15. A particulate matter detection device comprising:
a first electrode which has a plate-like shape and whose one surface is covered with a planar dielectric material; a second electrode disposed on the side of the one surface of the first electrode via a space through which a gas including a particulate matter flows, to perform the formation of an electric field and/or the discharge of electricity by a voltage applied between the first electrode and the second electrode; and a power source which applies the voltage; and
a measurement counter electrode disposed on the surface of a protruding dielectric material provided on the surface of the planar dielectric material and having a stepped portion with respect to the planar dielectric material; characteristic measurement means for measuring electric characteristics between the measurement counter electrode and the first electrode; and particulate matter amount calculation means for obtaining the amount of the particulate matter collected by the formation of the electric field and/or the discharge of the electricity, based on the change amount of the electric characteristics measured by the characteristic measurement means.

16. The particulate matter detection device according to claim 15, wherein the measurement counter electrode has a linear shape, and is disposed so as to be long in a direction vertical to a direction in which the gas including the particulate matter flows.

17. The particulate matter detection device according to claim 16, wherein the measurement counter electrode having the linear shape is disposed over the whole surface of the planar dielectric material while bending.

18. The particulate matter detection device according to claim 15, further comprising:
 a dielectric material which covers the other surface of the first electrode having the plate-like shape; and
 a heater disposed on the surface of the dielectric material.

19. The particulate matter detection device according to claim 15, further comprising:
 a power source for removal which applies a voltage between the first electrode and the measurement counter electrode to oxidize and remove the particulate matter by the discharge of the electricity along the surface,
 wherein the voltage is applied to perform the discharge of the electricity along the surface of the dielectric material which covers the one surface of the first electrode.

20. The particulate matter detection device according to claim 15, wherein the measurement counter electrode is covered with a film-like dielectric material.

* * * * *